United States Patent
Adler et al.

(10) Patent No.: US 8,927,210 B2
(45) Date of Patent: Jan. 6, 2015

(54) CONJUGATE COMPLEXES FOR ANALYTE DETECTION

(75) Inventors: Michael Adler, Langen-Debstedt (DE); Jan Detmers, Ovelgonne (DE)

(73) Assignee: Chimera Biotec GmbH, Dortmund (DE)

( * ) Notice: Subject to any disclaimer, the term of this patent is extended or adjusted under 35 U.S.C. 154(b) by 830 days.

(21) Appl. No.: 12/622,686

(22) Filed: Nov. 20, 2009

(65) Prior Publication Data

US 2010/0143925 A1 Jun. 10, 2010

Related U.S. Application Data

(60) Provisional application No. 61/116,648, filed on Nov. 21, 2008.

(51) Int. Cl.
| | | |
|---|---|---|
| *C12Q 1/68* | (2006.01) | |
| *G01N 33/53* | (2006.01) | |
| *C07H 21/00* | (2006.01) | |
| *C07K 14/00* | (2006.01) | |

(52) U.S. Cl.
CPC .............. *C12Q 1/6804* (2013.01); *C12Q 1/682* (2013.01)
USPC ........... 435/6.1; 435/7.1; 536/22.1; 536/23.1; 536/24.3; 530/350

(58) Field of Classification Search
USPC ................. 435/6.1, 7; 536/23.1, 24.3, 22.1; 530/350
See application file for complete search history.

(56) References Cited

U.S. PATENT DOCUMENTS

| | | | |
|---|---|---|---|
| 4,376,110 | A | 3/1983 | David et al. |
| 4,816,567 | A | 3/1989 | Cabilly et al. |
| 4,946,778 | A | 8/1990 | Ladner et al. |
| 5,565,332 | A | 10/1996 | Hoogenboom et al. |
| 5,635,352 | A * | 6/1997 | Urdea et al. ................. 435/6.18 |
| 5,658,727 | A | 8/1997 | Barabas et al. |
| 5,702,892 | A | 12/1997 | Mulligan-Kehoe |
| 5,723,287 | A | 3/1998 | Russell et al. |

(Continued)

FOREIGN PATENT DOCUMENTS

| | | |
|---|---|---|
| EP | 404097 | 6/1990 |
| EP | 844306 | 5/1998 |

(Continued)

OTHER PUBLICATIONS

Argarana et al., Molecular cloning and nucleotide sequence of the streptavidin gene. Nucleic Acids Research 14(4) : 1871 (1986).*

(Continued)

*Primary Examiner* — Ethan C Whisenant
(74) *Attorney, Agent, or Firm* — Michael A. Whittaker; Acuity Law Group, P.C.

(57) ABSTRACT

The present invention relates to novel conjugate complexes for immunoassays as well as kits comprising these conjugate complexes, methods of producing these complexes, and methods of detecting an analyte by use of these complexes. The conjugate complexes of the invention comprise one or more non-nucleic acid receptors capable of specifically binding an analyte, one or more nucleic acid markers comprising a predetermined nucleotide sequence, one or more first linker molecules capable of specifically binding the non-nucleic acid receptor and the nucleic acid marker, and one or more second linker molecules capable of specifically binding the first linker molecules.

30 Claims, 4 Drawing Sheets

(56) References Cited

U.S. PATENT DOCUMENTS

| | | | |
|---|---|---|---|
| 5,733,743 | A | 3/1998 | Johnson et al. |
| 5,750,373 | A | 5/1998 | Garrard et al. |
| 6,329,150 | B1* | 12/2001 | Lizardi et al. ............... 435/6.12 |
| 6,682,736 | B1 | 1/2004 | Hanson et al. |
| 2001/0041335 | A1* | 11/2001 | Goldberg et al. ................. 435/6 |
| 2004/0018495 | A1* | 1/2004 | Li ..................................... 435/6 |
| 2005/0089932 | A1 | 4/2005 | Kolkman et al. |
| 2005/0118580 | A1* | 6/2005 | Merk et al. ........................ 435/6 |
| 2008/0241865 | A1* | 10/2008 | Ohmiya et al. ................... 435/8 |
| 2008/0254516 | A1* | 10/2008 | St. John et al. ............. 435/91.2 |
| 2008/0254548 | A1* | 10/2008 | Bamdad et al. ................. 436/94 |
| 2008/0268061 | A1* | 10/2008 | Jordan et al. .................. 424/490 |
| 2008/0280778 | A1* | 11/2008 | Urdea ............................... 506/9 |
| 2008/0317839 | A1* | 12/2008 | Quay et al. .................... 424/450 |
| 2010/0143925 | A1* | 6/2010 | Adler et al. ........................ 435/6 |
| 2011/0111973 | A1* | 5/2011 | Mecklenburg et al. ........... 506/9 |

FOREIGN PATENT DOCUMENTS

| | | |
|---|---|---|
| WO | 9311161 | 6/1993 |
| WO | 9709436 | 3/1997 |
| WO | 9916873 | 4/1999 |
| WO | 0075308 | 2/2000 |
| WO | 03029462 | 4/2003 |
| WO | 03029463 | 4/2003 |
| WO | 03029471 | 4/2003 |
| WO | 2004009848 | 1/2004 |
| WO | 2005019254 | 3/2005 |
| WO | 2005019255 | 3/2005 |
| WO | 2005019256 | 3/2005 |
| WO | 2008036273 | 3/2008 |

OTHER PUBLICATIONS

Bartlett et al., Physicochemical and biological characterization of targeted, nucleic acid-containing nanoparticles. Bioconjugate Chemistry 18 :456 (2007).*
Davis et al., Self-Assembling Nucleic Acid Delivery Vehicles via Linear, Water-Soluble, Cyclodextrin-Containing Polymers. Current Medicinal Chemistry 11 : 179 (2004).*
Gonzales et al., New Class of Polymers for the Delivery of Macromolecular Therapeutics. Bioconjugate Chemistry 10 :1068 (1999).*
Hylarides et al., A robust method for the preparation and purification of antibody/streptavidin conjugates. Bioconjugate Chemistry 12 : 421 (2001).*
Pun et al. Development of a nonviral gene delivery vehicle for systemic application. Bioconjugate Chemistry 13 : 630 (2002).*
The Stratagene Catalog p. 39 (1988).*
Gosselin et al. Efficient gene transfer using reversibly cross-linked low molecular weight polyethylenimine. Bioconjugate Chemistry 12 :989 (2001).*
Nam et al., Nanoparticle-Based Bio-Bar Codes for the Ultrasensitive Detection of Proteins. Science 301 :1885 (2003).*
Adler et al. (2004) Current Technologies and Applictions, V.V. Demidov and N.E. Broude, Editors; Horizon Bioscience, Norfolk; p. 293-312.
Bird et al. (1988), Science 242: 423-26.
Cole, et al. (1985), in Monoclonal Antibodies and Cancer Therapy, Alan R. Liss, Inc., New York, pp. 77-96.
Cote, et al. (1983), Proc. Natl. Acad. Sci. USA, 80: 2026-30.
Harlow and Lane, eds. (1988) Antibodies—A Laboratory Manual. Cold Spring Harbor Laboratory, Chapter 6.
Heid et al. (1996) Genome Research, 6(10):986-994.
Hendrickson et al. (1995) Nucleic Acids Res., 23(3): 522-529.
Hollinger et al. (1993) Proc. Natl. Acad. Sci. USA, 90: 6444-6448.
Huse, et al. (1989), Science, 246: 1275-1281.
Huston, et al. (1988), Proc. Natl. Acad. Sci. USA, 85: 5879-83.
Ill et al. (1997) Protein Eng., 10:949-957.
Jones et al. (1986) Nature, 321: 522-525.
Köhler and Milstein (1975), Nature, 256: 495-7.
Kozbor, et al. (1983), Immunology Today, 4: 72.
Kukolka et al. (2004) Methods Mol. Biol. 283:181-196.
Maia et al. (1995) J. Virol. Methods, 52(3): 273-86.
Martin et al. (1994) EMBO J, 13:5303-9.
Morrison et al. (1984) Proc. Natl. Acad. Sci. USA, 81: 6851-6855.
Niemeyer et al. (1997) Anal. Biochem., 246(1):140-5.
Niemeyer et al. (2001) Bioconjugate Chem., 12:364-371.
Niemeyer et al., (2007) Nature Protocols 2(8):1918-1930.
Niemeyer et al. (2005) Trends Biotechnol., 23(4): 208-16.
Niemeyer et al. (1999) Nucleic Acids Research, 27(23):4553-4561.
Plueckthun (1994) The Pharmacology of Monoclonal Antibodies, vol. 113. Rosenburg and Moore eds. Springer-Verlag, New York, pp. 269-315.
Presta (1992) Curr. Op. Struct. Biol., 2: 593-596.
Rasmussen et al. (1998) Biochemica, 2:8-15.
Reichmann et al. (1988) Nature, 332: 323-329.
Ririe, K., et al. (1977) Anal. Biochem., 245: 154-160.
Sano et al. (2000) Science, 258(5079):120-122.
Silverman et al. (2005) Nature Biotechnology, 23(12):1556-61.
Traunecker et al. (1991) EMBO J., 10:3655-3659.
Traunecker et al. (1992) Int. J Cancer Suppl., 7:51-52.
Tyagi and Kramer (1996) Nat. Biotechnol, 14:303-308.
Tyagi et al. (2000) Nat Biotechnol, 18 : 1191-96.
Ward, et al. (1989) Nature, 334: 544-46.
Whitcombe et al. (1999) Nature Biotech, 17:804-807.
Wittwer et al. (1997) BioTechniques, 22: 176-181.
Wittwer et al. (1997) BioTechniques, 22: 130-138.
Zapata et al. (1995) Protein Eng., 8(10): 1057-1062.
Zhou et al. (1993) Nucleic Acids Res, 21(25): 6038-9.
Hill et al, "Nonenzymatic detection of bacterial genomic DNA using the bio bar code assay." Analytical Chemistry Dec. 1, 2007 LNKD—PUBMED:17927207, vol. 79, No. 23, Dec. 1, 2007, pp. 9218-9223, ISSN: 0003-2700.
Communication Pursuant to Article 94(3) EPC dated Aug. 18, 2010 issued in EP 09175511.6.

* cited by examiner

SEQUENCE LISTING

```
<160> NUMBER OF SEQ ID NOS: 8

<210> SEQ ID NO 1
<211> LENGTH: 169
<212> TYPE: DNA
<213> ORGANISM: artificial
<220> FEATURE:
<223> OTHER INFORMATION: DNA marker sequence 1

<400> SEQUENCE: 1
agcggataac aatttcacac aggaaacagc tatgaccatg attacgaatt cgagctcggt      60
acccggggat cctctagagt cgacctgcag gcatgcaagc ttggcactgg ccgtcgtttt     120
acaacgtcgt gactgggaaa accctggcgt tacccaactt aatcgcctt                 169

<210> SEQ ID NO 2
<211> LENGTH: 255
<212> TYPE: DNA
<213> ORGANISM: artificial
<220> FEATURE:
<223> OTHER INFORMATION: DNA marker sequence 2

<400> SEQUENCE: 2
tatgcagtgc tgccataacc atgagtgata acactgcggc caacttactt ctgacaacga      60
tcggaggacc gaaggagcta accgcttttt tgcacaacat gggggatcat gtaactcgcc     120
ttgatcgttg ggaaccggag ctgaatgaag ccataccaaa cgacgagcgt gacaccacga     180
tgcctgtagc aatggcaaca acgttgcgca aactattaac tggcgaacta cttactctag     240
cttcccggca acaat                                                      255

<210> SEQ ID NO 3
<211> LENGTH: 24
<212> TYPE: DNA
<213> ORGANISM: Artificial
<220> FEATURE:
<223> OTHER INFORMATION: Amplification primer

<400> SEQUENCE: 3
```

-continued

```
agcggataac aatttcacac agga                                          24

<210> SEQ ID NO 4
<211> LENGTH: 17
<212> TYPE: DNA
<213> ORGANISM: artificial
<220> FEATURE:
<223> OTHER INFORMATION: Amplification primer

<400> SEQUENCE: 4
aaggcgatta agttggg                                                  17

<210> SEQ ID NO 5
<211> LENGTH: 27
<212> TYPE: DNA
<213> ORGANISM: artificial
<220> FEATURE:
<223> OTHER INFORMATION: Amplification primer

<400> SEQUENCE: 5
attgttgccg ggaagctaga gtaagta                                       27

<210> SEQ ID NO 6
<211> LENGTH: 24
<212> TYPE: DNA
<213> ORGANISM: Artificial
<220> FEATURE:
<223> OTHER INFORMATION: Amplificiation primer

<400> SEQUENCE: 6
tatgcagtgc tgccataacc atga                                          24

<210> SEQ ID NO 7
<211> LENGTH: 24
<212> TYPE: DNA
<213> ORGANISM: Artificial
<220> FEATURE:
<223> OTHER INFORMATION: Hybridization sequence A

<400> SEQUENCE: 7
tcctgtgtga aattgttatc cgct                                          24

<210> SEQ ID NO 8
<211> LENGTH: 24
<212> TYPE: DNA
<213> ORGANISM: Artificial
<220> FEATURE:
<223> OTHER INFORMATION: Hybridization sequence cA

<400> SEQUENCE: 8
agcggataac aatttcacac agga                                          24
```

CONJUGATE COMPLEXES FOR ANALYTE DETECTION

CROSS-REFERENCE TO RELATED APPLICATIONS

The present invention claims priority to U.S. Provisional Patent Application No. 61/116,648 filed Nov. 21, 2008, which is hereby incorporated in its entirety, including all tables figures and claims.

FIELD OF THE INVENTION

The present invention lies in the field of immunology, molecular biology and molecular diagnostics and relates to the Immuno-PCR (polymerase chain reaction) technique. More specifically, the present invention relates to conjugate complexes for Immuno-PCR assays.

BACKGROUND OF THE INVENTION

Immunoassays where one or more antibodies are used to detect a test substance (target, analyte) in a test sample are widely known. A standard application of this technique is the Enzyme Linked Immunosorbent Assay ("ELISA"). The ELISA either uses a capture antibody immobilized on a solid surface for specifically capturing a target antigen from a complex biological matrix (sandwich immunoassay format) or the target antigen to be detected is non-specifically adsorbed to a solid surface, the solid surface typically being the inside of a microtiter plate well. Unbound matrix is removed by a washing step and subsequently followed by coupling of an enzyme-labelled detection antibody (direct ELISA) to the target or coupling of a detection antibody specific for the target antigen to the target followed by coupling of a secondary enzyme-labelled antibody to the primary antibody (indirect ELISA). The enzyme activity associated with the solid surface which is subsequently determined is directly proportional to the amount of bound antigen present and can be measured, for example, by using a chromogenic substrate for the enzyme.

The evolution of immunoassay methods increased the sensitivity of these tests by altering the detection principle. In the course of this development, the enzyme-coupled detection antibody was replaced by oligonucleotide (e.g. DNA) labelled antibodies. In these antibody-nucleic acid conjugates the oligonucleotide served as a marker that could be subsequently amplified and detected. In an application of the PCR ("polymerase chain reaction") as an exponential amplification system for nucleic acids to these antibody-based detection system (Sano et al. (2000), "Immuno-PCR: very sensitive antigen detection by means of specific antibody-DNA conjugates" Science 258(5079):120-122), the Immuno-PCR (IPCR) method was developed. The efficacy of this method was first demonstrated for the detection of Bovine Serum Albumin (BSA) as an antigen passively absorbed to an immuno-assay plate. Using an antibody specific for BSA coupled to a biotin-labeled reporter DNA plasmid by means of a protein A-avidin fusion protein, and subsequently utilizing 30 cycles of polymerase chain reaction (PCR) amplification to amplify the reporter DNA sequence, the detection of the amplicons by staining with ethidium bromide following gel electrophoresis was possible. Sano et al. (supra) reported an enhanced detection sensitivity of approximately five orders of magnitude when compared to ELISA detection. Theoretically, using this technique, a nucleic acid label when amplified by PCR or any other available exponential nucleic acid amplification technique can be detected with extraordinary sensitivity (potentially down to a single copy).

However, because of the liability of the protein A-avidin fusion protein to bind any antibody present, e.g. the capture antibody in a sandwich immunoassay, other means of attaching the DNA to the reporter antibody had to be found.

This was achieved by substituting the protein A-streptavidin fusion protein with a biotinylated detection antibody coupled to biotinylated DNA via sequential incubation of the antibody and the DNA with streptavidin as a tetravalent biotin-binding linker molecule (Zhou et al. (1993). "Universal Immuno-PCR for ultra-sensitive target protein detection." Nucleic Acids Res 21(25): 6038-9) or direct conjugates synthesized by covalently coupling antibodies and DNA (Hendrickson et al. (1995). "High Sensitivity Multianalyte Immunoassay Using Covalent DNA-Labeled Antibodies and Polymerase Chain Reaction." Nucleic Acids Res. 23(3): 522-529). With these strategies, a sandwich IPCR using antigen-specific capture and detection antibodies which was similar to conventional ELISA analysis and therefore able to detect antigens in complex biological matrices became accessible (Maia et al. (1995). "Development of a two-site immuno-PCR assay for hepatitis B surface antigen." J. Virol. Methods 52(3): 273-86).

Immuno-PCR is nowadays used in combination with several matrices for the detection of a number of different antigens, including virus particles, tumor markers or cytokines in various body fluids (Niemeyer et al. (2005) "Immuno-PCR: high sensitivity detection of proteins by nucleic acid amplification." Trends Biotechnol. 23(4): 208-16).

Due to the enormous exponential signal amplification, however, Immuno-PCR, as used in state of the art applications, is very susceptible to background effects by unspecific binding of sample contents and the involved reagents, especially during the antigen binding step. Since theoretically a single molecule of nucleic acid can be detected by PCR, failure to remove all of the non-specifically bound template DNA results in significant background compared to conventional ELISA techniques and interferes with the ability to detect minute quantities of analyte, because the signals from these unspecific binding events are amplified in IPCR, too. As well known among scientists working in this field, a background signal is, in contrast to other standard PCR techniques where signals for the negative control are typically not detectable, measured in all typical IPCR assays.

The art of improving IPCR assays is thereby mainly an attempt to either decrease the unavoidable background signal or to increase specific signals induced by the analyte in order to improve the signal-to-background ratio.

Niemeyer et al. (Niemeyer et al. (1999), Nucleic Acid Research 27(23): 4553-4561) have reported that the use of supramolecular antibody-modified DNA-STV oligomers as detection reagents in IPCR led to an enhanced sensitivity compared to the conventional IPCR procedure.

Nevertheless, there remains a need in the field of diagnostics and biosciences for strategies to further improve IPCR assay performance. Thus, one object of the inventors of the present invention was to provide an IPCR assay with further improved assay performance compared to known assays.

SUMMARY OF THE INVENTION

According to a first aspect, the present invention relates to a conjugate complex including:
(a) one or more non-nucleic acid receptors capable of specifically binding an analyte;

(b) one or more nucleic acid markers including a predetermined nucleotide sequence;

(c) one or more first linker molecules capable of binding the non-nucleic acid receptor and the nucleic acid marker; and (d) one or more second linker molecules capable of binding the first linker molecule.

In a further aspect, the present invention relates to methods for the preparation of the above conjugate complexes. In one embodiment, such a method for the preparation of a conjugate complex according to the invention includes the steps of:

(a) contacting one or more nucleic acid markers with one or more first linker molecules adapted to bind nucleic acid markers and non-nucleic acid receptors to form a complex of one or more nucleic acid markers with one or more first linker molecules;

(b) contacting the complex of step (a) with one or more non-nucleic acid receptors to form a complex of one or more non-nucleic acid receptors, one or more nucleic acid markers and one or more first linker molecules; and (c) contacting the complex of step (b) with one or more second linker molecules adapted to bind the first linker molecules to form a complex of one or more non-nucleic acid receptors, one or more nucleic acid markers, one or more first linker molecules and one or more second linker molecules.

This method may optionally further include the step of:

(d) contacting the complex of step (c) with one or more modulators adapted to bind to the first linker molecules to saturate non-occupied binding sites of the first linker molecule for the non-nucleic acid receptor, the nucleic acid marker and the second linker molecule to form a complex of one or more non-nucleic acid receptors, one or more nucleic acid markers, one or more first linker molecules, one or more second linker molecules and one or more modulators.

In another embodiment, the invention encompasses a method for the preparation of a conjugate complex including:

(i) one or more non-nucleic acid receptors capable of specifically binding an analyte;

(ii) one or more nucleic acid markers including a predetermined nucleotide sequence;

(iii) one or more first linker molecules adapted to bind the non-nucleic acid receptor and the nucleic acid marker;

(iv) one or more nucleic acid oligomers adapted to bind the first linker molecules, wherein the one or more nucleic acid oligomers comprise two complementary nucleic acid strands distinct from the nucleic acid marker; and (v) one or more organic polymers, polypeptides, polysaccharides or polynucleotides distinct from the nucleic acid marker and the one or more nucleic acid oligomers adapted to bind the first linker molecules;

wherein the method comprises the steps of:

(a) contacting one nucleic acid strand of the one or more nucleic acid oligomers with one or more first linker molecules to form a first conjugate of one or more first linker molecules and one nucleic acid strand of the one or more nucleic acid oligomers;

(b) contacting the nucleic acid strand of the one or more nucleic acid oligomers complementary to that used in step (a) with one or more first linker molecules to form a second conjugate of one or more first linker molecules and one nucleic acid strand of the one or more nucleic acid oligomers complementary to that used in step (a);

(c) contacting the conjugate of step (a) with one or more nucleic acid markers to form a first complex of one or more first linker molecules conjugated to one nucleic acid strand of the one or more nucleic acid oligomers and one or more nucleic acid markers;

(d) contacting the conjugate of step (b) with one or more non-nucleic receptors to form a second complex of one or more first linker molecules conjugated to one nucleic acid strand of the one or more nucleic acid oligomers complementary to that used in step (a) and (c) and one or more non-nucleic acid receptors;

(e) contacting the first complex of step (c) with one or more organic polymers, polynucleotides, polypeptides or polysaccharides, to form a third complex of one or more first linker molecules conjugated to one nucleic acid strand of the one or more nucleic acid oligomers, one or more nucleic acid markers and one or more organic polymers, polynucleotides, polypeptides or polysaccharides; and (f) contacting the second complex of step (d) with the third complex of step (e) to form a complex conjugate of one or more first linker molecules conjugated to one nucleic acid strand of the one or more nucleic acid oligomers, one or more nucleic acid markers, one or more organic polymers, polynucleotides, polypeptides or polysaccharides, one or more first linker molecules conjugated to one nucleic acid strand of the one or more nucleic acid oligomers complementary to that used in step (a) and (c) and one or more non-nucleic acid receptors.

In one embodiment of the invention, this method may further include the step of contacting the complexes of steps (d) and (e) with one or more modulators adapted to bind to the first linker molecule before step (f).

In another aspect, the invention is also directed to the use of the conjugate complex according to the invention in an immunoassay for the detection of an analyte.

In still another aspect, the invention features a method for detecting an analyte in a sample, wherein the method includes the steps of:

(a) contacting a conjugate complex according to the invention comprising one or more non-nucleic acid receptors capable of specifically binding said analyte with said sample to form a complex of said analyte and said conjugate complex;

(b) specifically detecting the presence of the one or more nucleic acid markers in said complex;

wherein the presence of the one or more nucleic acid markers indicates the presence of the analyte in said sample.

In another aspect, the invention relates to a kit including one or more conjugate complexes according to the invention or manufactured according to the methods of the invention. Such a kit may additionally contain further components, such as auxiliaries and excipients.

In still another aspect, the invention is also directed to the use of one or more organic polymer, polypeptide, polysaccharide and/or oligo- or polynucleotide molecules as additional linker molecules in a conjugate comprising one or more non-nucleic acid receptors, one or more nucleic acid markers and one or more first linker molecules to form a conjugate complex comprising one or more non-nucleic acid receptors, one or more nucleic acid markers, one or more first linker molecules and one or more organic polymer, polypeptide, polysaccharide and/or oligo- or polynucleotide molecules.

DETAILED DESCRIPTION OF THE INVENTION

Definitions

Figure 1:
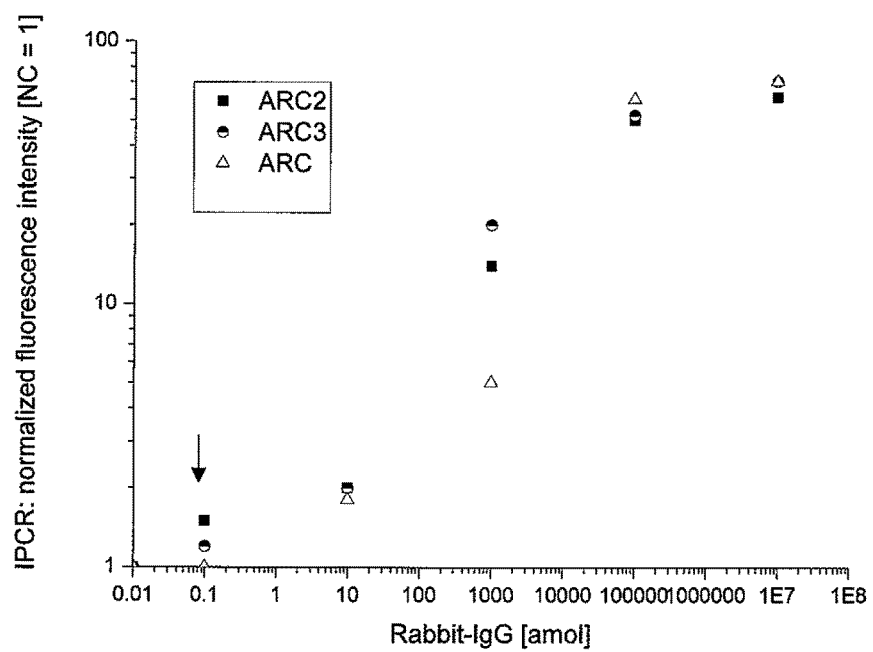
FIG. 1 shows the signal intensity of an IPCR assay for the detection of solid-phase immobilized rabbit IgG for different target concentrations and for anti-rabbit antibody-DNA-Streptavidin conjugates with and without additional polybiotinylated second linker molecules.

The terms used herein have, unless explicitly stated otherwise, the following meanings.

The term "one or more" as used herein in connection with molecules relates to at least one, but preferably at least 2, 3, 4, 5, 6, 7, 8, 9, 10, 12, 14, 15, 20, 25 or a plurality of molecules. In this connection, the term "plurality" means more than one, preferably 2-100, more preferably 2-50, still more preferably 2-25 and most preferably 2-15.

The term "non-nucleic acid receptor" as used herein refers to any molecule or fragment thereof capable of specifically binding to an analyte of choice so as to form a specific complex consisting of the molecule and the analyte.

"Specifically binding" and "specific binding" as used herein mean that the non-nucleic acid receptor molecule binds to the target analyte based on recognition of a binding region or epitope on the target molecule. The non-nucleic acid receptor preferably recognizes and binds to the target molecule with a higher binding affinity than it binds to other compounds in the sample. In various embodiments of the invention, "specifically binding" may mean that an antibody or other biological molecule, binds to a target molecule with at least about a $10^6$-fold greater affinity, preferably at least about a $10^7$-fold greater affinity, more preferably at least about a $10^8$-fold greater affinity, and most preferably at least about a $10^9$-fold greater affinity than it binds molecules unrelated to the target molecule. Typically, specific binding refers to affinities in the range of about $10^6$-fold to about $10^9$-fold greater than non-specific binding. In some embodiments, specific binding may be characterized by affinities greater than $10^9$-fold over non-specific binding. The binding affinity may be determined by any suitable method. Such methods are known in the art and include, without limitation, surface plasmon resonance and isothermal titration calorimetry. In a specific embodiment, the non-nucleic acid receptor uniquely recognizes and binds to the target analyte.

The non-nucleic acid receptor molecule may be a proteinaceous molecule, such as an antibody, for example a monoclonal antibody, which immunologically binds to the target analyte at a specific determinant or epitope. The term "antibody" is used in the broadest sense and specifically covers monoclonal antibodies as well as antibody variants or fragments (e.g., Fab, F(ab')$_2$, scFv, Fv diabodies and linear antibodies), so long as they exhibit the desired binding activity. For a review of scFv see Pluckthun (1994) The Pharmacology of Monoclonal Antibodies, Vol. 113. Rosenburg and Moore eds. Springer-Verlag, New York, pp. 269-315. Diabodies are described more fully in, for example, European patent 404097, international patent publication WO 93/11161 and Hollinger et al. (1993) Proc. Natl. Acad. Sci. USA 90: 6444-6448. Linear antibodies are described in Zapata et al. (1995) Protein Eng. 8(10): 1057-1062.

The term "monoclonal antibody" as used herein refers to an antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigenic site. Furthermore, in contrast to conventional (polyclonal) antibody preparations which typically include different antibodies directed against different determinants (epitopes), each monoclonal antibody is directed against a single determinant on the antigen. In addition to their specificity, the monoclonal antibodies are advantageous in that they may be synthesized by the hybridoma culture, uncontaminated by other immunoglobulins. The modifier "monoclonal" indicates the character of the antibody as being obtained from a substantially homogeneous population of antibodies, and is not to be construed as requiring production of the antibody by any particular method. The monoclonal antibodies can include "chimeric" antibodies (U.S. Pat. No. 4,816,567; and Morrison et al. (1984) Proc. Natl. Acad. Sci. USA, 81: 6851-6855) and humanized antibodies (Jones et al. (1986) Nature, 321: 522-525; Reichmann et al. (1988) Nature, 332: 323-329; Presta (1992) Curr. Op. Struct. Biol. 2: 593-596). A "chimeric" antibody is a molecule in which different portions are derived from different animal species, such as those having a variable region derived from a murine mAb and a human immunoglobulin constant region.

Monoclonal antibodies may be obtained by any technique that provides for the production of antibody molecules by continuous cell lines in culture. These include, but are not limited to the hybridoma technique of Koehler and Milstein (1975), Nature, 256: 495-7; and U.S. Pat. No. 4,376,110), the human B-cell hybridoma technique (Kosbor, et al. (1983), Immunology Today, 4: 72; Cote, et al. (1983), Proc. Natl. Acad. Sci. USA, 80: 2026-30), and the EBV-hybridoma technique (Cole, et al. (1985), in Monoclonal Antibodies And Cancer Therapy, Alan R. Liss, Inc., New York, pp. 77-96). The preparation of monoclonal antibodies specific for a target compound is also described in Harlow and Lane, eds. (1988) Antibodies—A Laboratory Manual. Cold Spring Harbor Laboratory, Chapter 6. Such antibodies may be of any immunoglobulin class including IgG, IgM, IgE, IgA, IgD and any subclass thereof. The hybridoma producing the mAb may be cultivated in vitro or in vivo. Production of high titers of mAbs in vivo makes this a very effective method of production.

"Polyclonal antibodies" are heterogeneous populations of antibody molecules derived from the sera of animals immunized with an antigen, or an antigenic functional derivative thereof. For the production of polyclonal antibodies, host animals such as rabbits, mice and goats, may be immunized by injection with an antigen or hapten-carrier conjugate optionally supplemented with adjuvants.

Alternatively, techniques described for the production of single chain antibodies (U.S. Pat. No. 4,946,778; Bird (1988), Science 242: 423-26; Huston, et al. (1988), Proc. Natl. Acad. Sci. USA, 85: 5879-83; and Ward, et al. (1989), Nature, 334:

544-46) can be adapted to produce gene-single chain antibodies. Single chain antibodies are typically formed by linking the heavy and light chain fragments of the Fv region via an amino acid bridge, resulting in a single chain polypeptide.

Antibody fragments that recognize specific epitopes may be generated by known techniques. For example, such fragments include but are not limited to: the F(ab')$_2$ fragments that can be produced by pepsin digestion of the antibody molecule and the Fab fragments that can be generated by reducing the disulfide bridges of the F(ab')$_2$ fragments. Alternatively, Fab expression libraries may be constructed (Huse, et al. (1989), Science, 246: 1275-1281) to allow rapid and easy identification of monoclonal Fab fragments with the desired specificity.

If an analyte is detected in a "sandwich" immunoassay, the detection may be carried out by using an identical polyclonal antibody as first binding ("capture") molecule and detection molecule ("non-nucleic acid receptor"). In this case, "identical" refers to the binding specificity only, and is defined as polyclonal antibodies from a single preparation, including antibodies against different binding sites of the target molecule. As the non-specific interaction of the polyclonal antibody with itself is minimized already during the genesis of the antibody, this approach may also be advantageous for minimization of assay background.

A variant of this approach is the use of an identical monoclonal antibody as capture and detection antibody if the target has several binding spots for this antibody, such as surface proteins in a virus shell, whereby in this application the virus shell would be the target. As above, "identical" in this connection only refers to the binding specificity of an antibody.

The non-nucleic acid receptor may also be any other proteinaceous scaffold that has been adapted or mutated to bind a given ligand with sufficient binding affinity.

Examples of useful scaffolds include those scaffolds described in US patent application 2005/0089932 or U.S. Pat. No. 6,682,736. Another example of suitable scaffolds are members of the lipocalin protein family as described in the international patent applications WO 99/16873, WO 00/75308, WO 03/029471, WO 03/029462, WO 03/029463, WO 2005/019254, WO 2005/019255 or WO 2005/019256, for instance.

In accordance with the above, scaffolds besides members of the lipocalin family include, but are not limited to, a EGF-like domain, a Kringle-domain, a fibronectin type I domain, a fibronectin type II domain, a fibronectin type III domain, a PAN domain, a Gla domain, a SRCR domain, a Kunitz/Bovine pancreatic trypsin Inhibitor domain, tendamistat, a Kazal-type serine protease inhibitor domain, a Trefoil (P-type) domain, a von Willebrand factor type C domain, an Anaphylatoxin-like domain, a CUB domain, a thyroglobulin type I repeat, LDL-receptor class A domain, a Sushi domain, a Link domain, a Thrombospondin type I domain, an immunoglobulin domain or a an immunoglobulin-like domain (for example, domain antibodies or camel heavy chain antibodies), a C-type lectin domain, a MAM domain, a von Willebrand factor type A domain, a Somatomedin B domain, a WAP-type four disulfide core domain, a F5/8 type C domain, a Hemopexin domain, an SH2 domain, an SH3 domain, a Laminin-type EGF-like domain, a C2 domain, "Kappabodies" (Ill. et al. "Design and construction of a hybrid immunoglobulin domain with properties of both heavy and light chain variable regions" Protein Eng 10:949-57 (1997)), "Minibodies" (Martin et al. "The affinity-selection of a minibody polypeptide inhibitor of human interleukin-6" EMBO J 13:5303-9 (1994)), "Janusins" (Traunecker et al. "Bispecific single chain molecules (Janusins) target cytotoxic lymphocytes on HIV infected cells" EMBO J 10:3655-3659 (1991) and Traunecker et al. "Janusin: new molecular design for bispecific reagents" Int J Cancer Suppl 7:51-52 (1992), a nanobody, a adnectin, a tetranectin, a microbody, an affilin, an affibody or an ankyrin, a crystallin, a knottin, ubiquitin, a zinc-finger protein, an autofluorescent protein, an ankyrin or ankyrin repeat protein or a leucine-rich repeat protein, an avimer (Silverman, Lu Q, Bakker A, To W, Duguay A, Alba B M, Smith R, Rivas A, Li P, Le H, Whitehorn E, Moore K W, Swimmer C, Perlroth V, Vogt M, Kolkman J, Stemmer W P 2005, Nat Biotech) (Nat Biotechnol. 2005 Nov. 20 edition, e-published before print); as well as multivalent avimer proteins evolved by exon shuffling of a family of human receptor domains as also described in Silverman J, Lu Q, Bakker A, To W, Duguay A, Alba B M, Smith R, Rivas A, Li P, Le H, Whitehorn E, Moore K W, Swimmer C, Perlroth V, Vogt M, Kolkman J, Stemmer W P, Nat. Biotechnology. 2005 December; 23(12):1556-61.

As mentioned above, in certain embodiments of the invention the non-nucleic acid receptor may be a mutein of the member of the lipocalin protein family. In some of these embodiments, the open end of the β-barrel structure of the lipocalin fold (which encompasses the natural ligand binding site of the lipocalin family) is used to form the target analyte binding site. Members of the lipocalin family of proteins include, but are not limited to the bilin binding protein of *Pieris brassicae* (SWISS-PROT Data Bank Accession Number P09464), human tear lipocalin (SWISS-PROT Data Bank Accession Number M90424), human apolipoprotein D (SWISS-PROT Data Bank Accession Number P05090), the retinol binding protein (RBP) (for example of human or porcine origin, SWISS-PROT Data Bank Accession Number of the human RBP: P02753, SWISS-PROT Data Bank Accession Number of the porcine RBP P27485), human neutrophil gelatinase-associated lipocalin (hNGAL, SWISS-PROT Data Bank Accession Number P80188), rat $\alpha_2$-microglobulin-related protein (A2m, (SWISS-PROT Data Bank Accession Number P31052), and mouse 24p3/uterocalin (24p3, (SWISS-PROT Data Bank Accession Number P11672), Von Ebners gland protein 2 of *Rattus norvegicus* (VEG protein 2; SWISS-PROT Data Bank Accession Number P41244), Von Ebners gland protein 2 of *Sus scrofra* (pig) (LCN1; SWISS-PROT Data Bank Accession Number P53715), the Major allergen Can f1 precursor of dog (ALL 1, SWISS-PROT Data Bank Accession Number O18873), and insecticyanin A or insecticyanin B of the tobacco hawkmoth *Manducta sexta* (SWISS-PROT Data Bank Accession Number P00305 and Q00630, respectively).

The non-nucleic acid receptor may also be a binding protein, receptor or extracellular domain (ECD) thereof capable of forming a binding complex with a ligand, typically a polypeptide or glycopeptide ligand.

The non-nucleic acid receptor may also be a phage-antibody. Antibodies and antibody fragments may be displayed on the surface of a filamentous bacteriophage as described in U.S. Pat. No. 5,750,373, for example and the references cited therein. See also EP 844306; U.S. Pat. No. 5,702,892; U.S. Pat. No. 5,658,727; WO 97/09436; U.S. Pat. No. 5,723,287; U.S. Pat. No. 5,565,332; and U.S. Pat. No. 5,733,743.

Those skilled in the art will recognized that the non-limiting examples given above describing various forms of antibodies as non-nucleic acid receptors can also be extended to other proteinaceous receptors such as recombinant, chimeric, hybrid, truncated etc., forms of non-antibody receptors.

The term "nucleic acid marker" or "nucleic acid reporter" refers to a nucleic acid molecule that will produce a detection product of a predicted size or other selected characteristic when used with appropriately designed oligonucleotide primers in a nucleic acid amplification reaction, such as a PCR reaction, preferably a real time PCR reaction. Skilled artisans will be familiar with the design of suitable oligonucleotide primers for PCR and programs are available, for example, over the Internet to facilitate this aspect of the invention (See, for example, http://bibiserv.techfak.uni-bielefeld.de/genefisher2/). A nucleic acid marker may be linear or circular. In specific embodiments, the nucleic acid marker will comprise a predetermined, linear nucleic acid sequence with binding sites for selected primers located at or near each end. In a circular DNA nucleic acid molecule, the primers will be internal rather than at an end, and a single primer may be used, e.g. for Rolling Circle Amplification. Amplified DNA may be detected using any available method, including, but not limited to techniques such as labeled oligonucleotide probes, SYBR Green or ethidium bromide staining or electrochemical methods. In certain embodiments, the DNA sequence located between the primer binding sites comprises a "characteristic identification sequence" capable of being detected during the PCR reaction. Fluorescent signal generation may, for example, be sequence-specific (Molecular Beacons, Taq Man, Scorpions, fluorogenic primers, such as the LUX primers (Invitrogen (Carlsbad, Calif.)) or mass dependent (SYBR Green, Ethidium Bromide). The examples provided are not meant to be an exhaustive list of possible nucleic acid detection schemes as those skilled in the art will be aware of alternative markers suitable for use in the methods of the present invention.

The term "characteristic identification sequence" refers to a nucleic acid sequence that can be specifically detected by virtue of hybridization to oligonucleotide or other nucleic acid that has been labeled with a detectable marker such as a radioisotope, a dye (such as a fluorescent dye), or other species that will be known in the art. In some embodiments, the characteristic identification sequence is capable of binding a "molecular beacon" probe. The term "molecular beacon" refers to oligonucleotides such as those sold by Operon Technologies (Alameda, Calif., USA) and Synthetic Genetics (San Diego, Calif., USA). (See also, Tyagi and Kramer (1996), Nat. Biotechnol, 14: 303-308; and Tyagi et al. (2000), Nat Biotechnol, 18: 1191-96). In another specific embodiment, the identification sequence is capable of binding a Scorpion. "Scorpions" are bifunctional molecules containing a PCR primer covalently linked to a probe. The fluorophore in the probe interacts with a quencher which reduces fluorescence. During a PCR reaction the fluorophore and quencher are separated which leads to an increase in light output from the reaction tube. Scorpions are sold by DxS Ltd. (Manchester, UK). As noted herein, a signal can be generated using a variety of techniques and reagents.

The terms "polynucleotide" and "nucleic acid (molecule)" are used interchangeably to refer to polymeric forms of nucleotides of any length, including naturally occurring and non-naturally occurring nucleic acids. The polynucleotides may contain deoxyribonucleotides, ribonucleotides and/or their analogs. Methods for selection and preparation of nucleic acids are diverse and well described in standard biomolecular protocols. A typical way would be preparative PCR and chromatographic purification starting from existing template DNAs or stepwise synthesis of artificial nucleic acids.

Nucleotides may have any three-dimensional structure, and may perform any function, known or unknown. The term "nucleic acid molecule" includes single-, double-stranded and triple helical molecules. "Oligonucleotide" refers to polynucleotides of between 3 and about 100, for example 3-50, 5-30, or 5-20 nucleotides of single- or double-stranded nucleic acid, typically DNA.

Oligonucleotides are also known as oligomers or oligos and may be isolated from genes, or chemically synthesized by methods known in the art. A "primer" refers to an oligonucleotide, usually single-stranded, that provides a 3'-hydroxyl end for the initiation of enzyme-mediated nucleic acid synthesis.

The following are non-limiting embodiments of nucleic acids: a gene or gene fragment, exons, introns, mRNA, tRNA, rRNA, ribozymes, cDNA, recombinant polynucleotides, branched polynucleotides, plasmids, vectors, isolated DNA of any sequence, isolated RNA of any sequence, nucleic acid probes and primers. A nucleic acid molecule may also comprise modified nucleic acid molecules, such as methylated nucleic acid molecules and nucleic acid molecule analogs. Analogs of purines and pyrimidines are known in the art, and include, but are not limited to, aziridinylcytosine, 4-acetylcytosine, 5-fluorouracil, 5-bromouracil, 5-carboxymethylaminomethyl-2-thiouracil, 5-carboxymethyl-aminomethyluracil, inosine, N6-isopentenyladenine, 1-methyladenine, 1-methylpseudouracil, 1-methylguanine, 1-methylinosine, 2,2-dimethylguanine, 2-methyladenine, 2-methylguanine,3-methylcytosine,5-methylcytosine, pseudouracil, 5-pentylnyluracil and 2,6-diaminopurine. The use of uracil as a substitute for thymine in a deoxyribonucleic acid is also considered an analogous form of pyrimidine. A nucleic acid may also include a backbone modification, wherein the phosphodiester bonds are replaced with phosphorothioates or methylphosphonates.

The term "linker" or "linker molecule" refers to a molecule that either links the nucleic acid marker to the non-nucleic acid receptor and thus facilitates detection of an analyte specifically bound by the non-nucleic acid receptor via detecting the nucleic acid marker or that interconnects other linker molecules. The linker molecules according to the present invention are chemically distinct from the non-nucleic acid receptor and the nucleic acid marker and are capable of binding the non-nucleic acid receptor and the nucleic acid marker and/or other, chemically different linker molecules. To achieve formation of a conjugate complex according to the invention, the linker molecules of the invention are at least bivalent, preferably trivalent, tetravalent, pentavalent, hexavalent or multivalent. In this connection, the term "multivalent" relates to linker molecules that can bind more than 2, preferably more than 3 other molecules. The multiple molecules bound by the linker molecules may be the same or different. For example, a linker molecule may have binding sites for the nucleic acid marker, the non-nucleic acid receptor and/or another, chemically different linker molecule or, alternatively, 2, 3, 4 or more binding sites for one specific binding partner. In the latter case, complex formation is achieved by coupling one or more binding partner(s) to other components of the conjugate complex, such as the nucleic acid marker, the non-nucleic acid receptor and another, chemically different linker molecule. In this connection, the expression "binding partner" relates to a molecule which is specifically recognized and bound by a linker molecule. The binding partner may thus be a small organic molecule, but can also be any other molecule, such as, for example, a peptide, polypeptide, protein, saccharide, polysaccharide or a lipid or an antigen or hapten. Specific examples for such a pair of linker molecule and binding partner are the streptavidin/biotin and avidin/biotin binding pairs. If the linker molecule is streptavidin/avidin and the binding partner is biotin, the biotin may be coupled to either one or all of the non-nucleic acid receptor, the nucleic acid marker and the second linker molecule to facilitate conjugate complex formation. The binding of the linker molecule to its binding partner and/or the nucleic acid marker, the non-nucleic acid receptor and/or other, chemically distinct linker molecules is preferably non-covalent. The linker molecules according to the invention may comprise one or more molecules selected from the group consisting of polysaccharides, organic polymers, polypeptides and nucleic acids distinct from the nucleic acid marker. In case the linker molecule according to the invention comprises a nucleic acid distinct from the nucleic acid marker, the linker molecule may further comprise a polysaccharide, organic polymer or polypeptide chemically coupled to the nucleic acid part.

The terms "analyte", "target compound", "target molecule" or "target" as interchangeably used herein, refer to any substance that can be detected in an assay by binding to a binding molecule, and which may be present in a sample. Therefore, the analyte can be, without limitation, any substance for which there exists a naturally occurring antibody or for which an antibody can be prepared. The analyte may, for example, be an antigen, a protein, a polypeptide, a hapten, a carbohydrate, a lipid, a cell or any other of a wide variety of biological or non-biological molecules, complexes or combinations thereof. Generally, the analyte will be a protein, peptide, carbohydrate or lipid derived from a biological source such as bacterial, fungal, viral, plant or animal samples. Additionally, however, the target may also be a small organic compound such as a drug, drug-metabolite, dye or other small molecule present in the sample.

When small molecules are the target compound, a competitive assay, including a competitive incubation step of the target compound to be analysed as present in the sample, an added modified variant of the target compound as a "competitor", and a binding molecule, can be used. In a specific embodiment of the competitive assay, the first binding molecule of the assay is specific for the target compound while the detection component is specific for the modification of the added competitor. In another embodiment, the competitor is immobilized on the solid phase and incubated with the target-containing sample and the binding molecule.

Analytes of the invention may comprise a nucleic acid component, but in such cases the binding of the analyte to be detected is not dependent on complementary hybridization between a target nucleic acid sequence in the analyte and a nucleic acid sequence used for detection, such as a detection probe.

The term "sample", as used herein, refers to an aliquot of material, frequently biological matrices, an aqueous solution or an aqueous suspension derived from biological material. Samples to be assayed for the presence of an analyte by the methods of the present invention include, for example, cells, tissues, homogenates, lysates, extracts, and purified or partially purified proteins and other biological molecules and mixtures thereof.

Non-limiting examples of samples typically used in the methods of the invention include human and animal body fluids such as whole blood, serum, plasma, cerebrospinal fluid, sputum, bronchial washing, bronchial aspirates, urine, semen, lymph fluids and various external secretions of the respiratory, intestinal and genitourinary tracts, tears, saliva, milk, white blood cells, myelomas and the like; biological fluids such as cell culture supernatants; tissue specimens which may or may not be fixed; and cell specimens which may or may not be fixed. The samples used in the methods of the present invention will vary based on the assay format and the nature of the tissues, cells, extracts or other materials, especially biological materials, to be assayed. Methods for preparing protein extracts from cells or samples are well known in the art and can be readily adapted in order to obtain a sample that is compatible with the methods of the invention.

"Peptide" generally refers to a short chain of amino acids linked by peptide bonds. Typically peptides comprise amino acid chains of about 2-100, more typically about 4-50, and most commonly about 6-20 amino acids. "Polypeptide" generally refers to individual straight or branched chain sequences of amino acids that are typically longer than peptides. "Polypeptides" usually comprise at least about 20 to 1000 amino acids in length, more typically at least about 100 to 600 amino acids, and frequently at least about 200 to about 500 amino acids. Included are homo-polymers of one specific amino acid, such as for example, poly-lysine. "Proteins" include single polypeptides as well as complexes of multiple polypeptide chains, which may be the same or different.

Multiple chains in a protein may be characterized by secondary, tertiary and quaternary structure as well as the primary amino acid sequence structure, may be held together, for example, by disulfide bonds, and may include post-synthetic modifications such as, without limitation, glycosylation, phosphorylation, truncations or other processing.

Antibodies such as IgG proteins, for example, are typically comprised of four polypeptide chains (i.e., two heavy and two light chains) that are held together by disulfide bonds. Furthermore, proteins may include additional components such associated metals (e.g., iron, copper and sulfur), or other moieties. The definitions of peptides, polypeptides and proteins includes, without limitation, biologically active and inactive forms; denatured and native forms; as well as variant, modified, truncated, hybrid, and chimeric forms thereof.

The term "organic polymers", as used herein, refers to polymers of organic molecules, preferably including functional groups such as hydroxy, amino, imino, nitro, cyano, carboxy, carbonyl, carbamid, halo, acylhalo, aldehyde, epoxy, and/or thiol groups. Exemplary polymers are, for example, polyethyleneimines, poly(meth)acrylamides, polyamines, polyamidoamines, polyethyleneglycols, polyethylene, polypropylene, poly(meth)acrylates, polyurethanes, polystyrenes, and polyesters. Preferred are cationic polymers, such as those having amino or imino groups, such as, for example, polyethyleneimines, poly(meth)acrylamides, polyamines, and polyamidoamines. The organic polymers may be linear, branched or dendritic.

The term "polysaccharide" refers to molecules consisting of at least two monosaccharides linked by a glycosidic bond and includes disaccharides and oligosaccharides. Exemplary polysaccharides are starch, glycogen, dextran, cellulose and chitin. The polysaccharides according to the invention may be linear, branched or dendritic polysaccharides.

The terms "contacting" or "incubating" as used interchangeably herein refer generally to providing access of one component, reagent, analyte or sample to another. For example, contacting can involve mixing a solution comprising a non-nucleic acid receptor with a sample. The solution comprising one component, reagent, analyte or sample may also comprise another component or reagent, such as dimethyl sulfoxide (DMSO) or a detergent, which facilitates mixing, interaction, uptake, or other physical or chemical phenomenon advantageous to the contact between components, reagents, analytes and/or samples. In one embodiment of the invention, contacting involves adding a solution comprising a non-nucleic acid receptor to a sample utilizing a delivery apparatus, such as a pipette-based device or syringe-based device.

The term "detecting" as used herein refers to any method of verifying the presence of a given molecule. The techniques used to accomplish this may include, but are not limited to, PCR, sequencing, PCR sequencing, molecular beacon technology, Scorpions technology, hybridization, and hybridization followed by PCR. Examples of reagents which might be used for detection include, but are not limited to, radio-labeled and fluorescently oligonucleotide probes and dyes, such as DNA intercalating dyes.

The term "hapten" as used herein, refers to a small proteinaceous or non-protein antigenic determinant which is capable of being recognized by an antibody. Typically, haptens do not elicit antibody formation in an animal unless part of a larger species. For example, small peptide haptens are frequently coupled to a carrier protein such as keyhole limpet hemocyanin in order to generate an anti-hapten antibody response.

"Antigens" are macromolecules capable of generating an antibody response in an animal and being recognized by the resulting antibody. Both antigens and haptens comprise at least one antigenic determinant or "epitope", which is the region of the antigen or hapten which binds to the antibody. Typically, the epitope on a hapten is the entire molecule.

The term "conjugate" as used herein refers to two or more molecules which have been linked together. The linkage to each other may be covalent or non-covalent. One example of a conjugate according to the invention is a conjugate consisting of a non-nucleic acid receptor and a nucleic acid marker, non-covalently linked to each other by means of a first linker molecule. In a particular embodiment, the conjugate comprises, consists essentially of or consists of a biotinylated DNA molecule coupled via a streptavidin molecule to an analyte-specific biotinylated antibody. Such a conjugate may be an oligomeric conjugate, i.e. comprise more than one nucleic acid marker and/or more than one non-nucleic acid receptor and/or more than one first linker molecules.

The term "conjugate complex", as used herein, refers to a complex of one or more non-nucleic acid receptors, one or more nucleic acid markers, one or more linker molecules of a first type, and one or more linker molecules of a second type. In one embodiment, the conjugate complexes according to the invention may comprise two or more conjugates as defined above and additionally one or more second linker molecule(s). In one specific embodiment of the invention, such a conjugate complex according of the invention comprises at least two non-nucleic acid receptors and at least two nucleic acid markers, non-covalently linked to each other by means of at least two first and at least two second linker molecules. In a particular embodiment, the conjugate complex comprises, consists essentially of or consists of at least one, for example 2 or more, biotinylated DNA molecule(s) coupled via at least one, preferably two or more, streptavidin molecule(s) and at least one, preferably to or more, biotinylated organic polymer or protein molecules, such as BSA, polyethyleneimines, poly(meth)acrylamides, polyamines, or polyamidoamines, to at least one, preferably two or more, analyte-specific biotinylated antibody/antibodies. In a particular embodiment, the conjugate complex comprises, consists essentially of or consists of one or more, preferably at least two (bis-)biotinylated DNA marker molecule(s) coupled via one or more, preferably at least two streptavidin molecule(s) and one or more, preferably at least two poly-biotinylated organic polymer(s) or protein(s)/polypeptide(s), such as BSA, polyethyleneimines, poly(meth)acrylamides, polyamines, or polyamidoamines, to one or more, preferably at least two analyte-specific poly-biotinylated antibodies. In this connection, "poly-biotinylated" refers to covalent modification with two or more biotin moieties.

PREFERRED EMBODIMENTS

The instant invention is based on the inventors' surprising finding that by use of conjugate complexes that consist of, consist essentially of or comprise one or more non-nucleic acid receptors, one or more nucleic acid markers, one or more first linker molecules adapted to bind the non-nucleic acid receptor and the nucleic acid marker, and one or more second linker molecules adapted to bind the first linker molecule the performance, in particular the assay sensitivity and the signal-to-background-ratio, of an Immuno-PCR ("IPCR") reaction can be significantly improved.

Thus, in a first aspect, the invention relates to conjugate complexes comprising one or more non-nucleic acid receptors, one or more nucleic acid markers, one or more first linker molecules adapted to bind the non-nucleic acid receptor and the nucleic acid marker, and one or more second linker molecules adapted to bind the first linker molecule. In one specific embodiment of the present invention, the conjugate complexes comprise a plurality of non-nucleic acid receptors, nucleic acid markers, first linker molecules and second linker molecules. It is desirable to include several non-nucleic acid receptors with specific binding affinity for a certain analyte in the conjugate complexes according to the invention in order to enhance the affinity for the analyte of choice by means of increased avidity. In turn, it is also desirable to include several nucleic acid markers in the conjugate complexes, because thus the positive signal, indicating the presence of the analyte in a sample, is enhanced and the signal-to-background ratio improved.

In the conjugate complexes according to the present invention, the first and second linker molecules serve the purpose to form supramolecular aggregates of the non-nucleic acid receptors and the nucleic acid markers and thus increase the sensitivity of the complexes as detection reagents in IPCR assays. To achieve the self-assembly of supramolecular networks, the first linker molecules are adapted to bind the non-nucleic acid receptors, the nucleic acid markers and the second linker molecules.

The supramolecular conjugate complexes according to the present invention may include 2-50, preferably 5-50 molecules of each the non-nucleic acid receptors, the nucleic acid markers, the first linker molecules and the second linker molecules. In one embodiment of the invented conjugate complexes, the complexes include at least 2, preferably 3 or more non-nucleic acid receptors and/or nucleic acid markers. In some embodiments of the invention, the invented conjugate complexes include about 10-40 nucleic acid marker and first linker molecules, about 5-15 non-nucleic acid receptor molecules and about 5-10 second linker molecules.

In accordance with one embodiment of the present invention, the non-nucleic acid receptor may be an antibody or antibody fragment that retains the ability to specifically bind an analyte of interest. The antibody may be a monoclonal or polyclonal antibody and the antibody fragment may be, for example, a Fab or F(ab')$_2$ fragment, a single chain variable fragment (scFv), an Fv diabody or a linear antibody. Alternatively, the non-nucleic acid receptor may be a protein other than an antibody, such as, for example a protein domain or a proteinaceous scaffold molecule with sufficient binding affinity for the analyte of choice. Such protein domains are known in the art and include, for example, the extracellular domains of cellular receptors or domains involved in intracellular signalling pathways, such as SH2, SH3 and PH domains and the like. Suitable proteinaceous scaffolds are also known in the art and include, but are not limited to, muteins of the lipocalin family of proteins, such as muteins of human tear lipocalin, human neutrophil gelatinase associated lipocalin, human retinol-binding protein, apolipoprotein D and bilin-binding protein. Further embodiments of the non-nucleic acid receptor have been defined above. All of the above non-nucleic acid receptors may be biotinylated and thus include one or more biotin or biotin analog moieties.

The nucleic acid marker including a predetermined nucleotide sequence may be any nucleic acid, such as, for example, double- or single-stranded DNA, double- or single stranded RNA, or double-stranded hybrids of DNA and RNA. The nucleic acid marker may contain nucleotide analogs, such as those, in which the naturally occurring bases and sugars are replaced by base analogs or sugar analogs or in which the phosphate backbone is substituted by other suitable groups. Suitable modifications have been mentioned above. All aforementioned nucleic acid marker molecules may be biotinylated and thus include one or more biotin or biotin analog moieties. One particular example are mono- or bis-biotinylated DNA molecules.

In one embodiment of the invention, the conjugate complexes are formed by non-covalent interactions between the first linker molecules and the non-nucleic acid receptor and/or the nucleic acid marker. In such an embodiment, the binding of the first linker molecule to the second linker molecule may also be non-covalent.

According to one specific embodiment of the present invention, the binding of the first linker molecule to the non-nucleic acid receptor, the nucleic acid marker and/or the second linker molecule may be facilitated by coupling each the non-nucleic acid receptor, the nucleic acid marker and/or the second linker molecule to one or more, for example 2, 3, 4, 5 or more binding partners of the first linker molecule. These binding partners may be the same or different for the non-nucleic acid receptor, the nucleic acid marker and the second linker molecule. In one embodiment of the invention, these binding partners of the first linker molecule are covalently coupled to the non-nucleic acid receptor, the nucleic acid marker and/or the second linker molecule.

In accordance with one specific embodiment of the present invention, the binding partner of the first linker molecule may be a ligand of the first linker molecule. It is preferred that the first linker molecule is bivalent, trivalent, tetravalent or multivalent for the binding to the binding partner. In one embodiment, the first linker molecule specifically recognizes and binds its binding partner with a high affinity.

In one embodiment of the present invention, the first linker molecule may be avidin or streptavidin or a biotin-binding fragment or mutant thereof.

In a specific embodiment, the binding partner of the first linker molecule is biotin or a biotin analog. The biotin analogs of the present invention preferably retain the ability to specifically bind to avidin, streptavidin or a biotin-binding fragment or mutant thereof.

If the first linker molecule is avidin, streptavidin or a biotin-binding fragment or mutant thereof, the binding of the first linker molecule to the non-nucleic acid receptor, the nucleic acid marker and/or the second linker molecule may be facilitated by coupling the non-nucleic acid receptor, the nucleic acid marker and/or the second linker molecule to biotin or a biotin analog. This coupling may be covalent and either of the non-nucleic acid receptor, the nucleic acid marker and/or the second linker may be coupled to at least 2 biotin or biotin analog molecules.

In an alternative embodiment, the first linker molecule may be a fusion protein or an at least bivalent antibody or antibody-like molecule adapted to simultaneously bind at least two of the non-nucleic acid receptor, the nucleic acid marker and the second linker molecule.

According to one embodiment of the invention, the second linker molecules may be selected from the group consisting of nucleic acids distinct from the nucleic acid marker, organic polymers, polypeptides and polysaccharides. In one embodiment of the present invention, the second linker molecules comprise at least two, three or four different molecules selected from the group consisting of nucleic acids distinct from the nucleic acid marker, organic polymers, proteins and polysaccharides.

If the second linker molecules consist of, consist essentially of or include organic polymer molecules, these may be selected from the group consisting of cationic polymers, such as linear, branched or dendritic polyethyleneimines, polyacrylamides, polyamines, and polyamidoamines according to one specific embodiment of the present invention.

In case the second linker molecules consist of, consist essentially of or include protein or polypeptide molecules, these may be selected from the group consisting of serum albumines and immunoglobulins or fragments thereof. In one embodiment, the second linker molecule may be BSA. Alternatively, the second linker molecules may be homo-polymers of cationic amino acids, such as poly-lysine, poly-histidine or poly-arginine.

In one alternative embodiment of the present invention, the second linker molecules consist of, consist essentially of or include polysaccharides selected from the group consisting of linear, cyclic or branched dextrans.

In still another embodiment of the present invention, the second linker molecules may also consist of, consist essentially of or include nucleic acid molecules distinct from the nucleic acid marker. The nucleic acid molecules may be nucleic acid oligomers, for example, oligonucleotides or nucleic acid polymers, such as polynucleotides. Exemplary nucleic acid oligomers that may be used as second linker molecules consist of two complementary nucleic acid strands, wherein each of these strands is independently adapted to bind to a first linker molecule. In one specific embodiment of the invention, this binding to a first linker molecule is facilitated by covalently coupling each single strand of the nucleic acid oligomer to one first linker molecule, with the result that each of these two strands is independently coupled to a first linker molecule by a covalent bond.

Another alternative embodiment may be a polynucleotide adapted to bind one or more first linker molecules.

In one embodiment of the present invention, the second linker molecules may also be a heterogeneous mixture of the above specified molecules. According to one embodiment of the present invention, the second linker molecules thus include two or more different molecules selected from the group consisting of linear, branched or dendritic polyethyleneimines, polyacrylamides, polyamines, polyamidoamines, homo-polymers of cationic amino acids, such as poly-lysine, serum albumines, immunoglobulins or fragments thereof, linear, cyclic or branched dextrans, poly- and oligonucleotides. In one specific embodiment of the present invention, the second linker molecules include nucleic acid oligomers consisting of two complementary nucleic acid strands, wherein each of these strands is independently adapted to bind to a first linker molecule, optionally be forming a covalent bond, and organic polymers, such as polyethyleneimines, polypeptides, such as albumines or immunoglobulins, polysaccharides and/or polynucleotides distinct from the nucleic acid oligomers and the nucleic acid marker.

All afore-mentioned second linker molecules may be coupled to one or more biotin or biotin analog molecules. Specific examples of second linker molecules according to the invention are polybiotinylated BSA, polybiotinylated polyethyleneimine, polybiotinylated poly(meth)acrylamide, polybiotinylated polyamine, or polybiotinylated polyamidoamine.

The analyte which is specifically recognized and bound by the non-nucleic acid receptor may be an antigen or hapten. The antigen may, for example, be a protein, a polypeptide, a carbohydrate, a lipid, a small organic compound, a cell or any other of a wide variety of biological or non-biological molecules, complexes or combinations thereof.

In one embodiment of the present invention, the conjugate complexes of the invention may further include one or more modulators adapted to bind to the first linker molecules. These modulators are used to saturate non-occupied binding sites of the first linker molecule for the non-nucleic acid receptor, the nucleic acid marker, the second linker molecule and/or a binding partner of the first linker molecule. In order to avoid that the modulators compete with the binding of the non-nucleic acid receptor, the nucleic acid marker, the second linker molecule and/or a binding partner of the first linker molecule coupled to the non-nucleic acid receptor, the nucleic acid marker and/or the second linker molecule, the modulator is preferably added after formation of a conjugate complex from the non-nucleic acid receptor, the nucleic acid marker, the first and the second linker molecule. The modulators may be positively charged and may be selected from the group consisting of amino-biotin, diamino-biotin and amino-substituted biotin analogs.

In a further aspect, the present invention relates to methods for the preparation of the above conjugate complexes. In one embodiment, such a method for the preparation of a conjugate complex according to the invention includes the steps of:

(a) contacting one or more nucleic acid markers with one or more first linker molecules adapted to bind nucleic acid markers and non-nucleic acid receptors to form a complex of one or more nucleic acid markers with one or more first linker molecules;

(b) contacting the complex of step (a) with one or more non-nucleic acid receptors to form a complex of one or more non-nucleic acid receptors, one or more nucleic acid markers and one or more first linker molecules; and (c) contacting the complex of step (b) with one or more second linker molecules adapted to bind the first linker molecules to form a complex of one or more non-nucleic acid receptors, one or more nucleic acid markers, one or more first linker molecules and one or more second linker molecules.

This method may optionally further include the step of:

(d) contacting the complex of step (c) with one or more modulators adapted to bind to the first linker molecules to saturate non-occupied binding sites of the first linker molecule for the non-nucleic acid receptor, the nucleic acid marker and the second linker molecule to form a complex of one or more non-nucleic acid receptors, one or more nucleic acid markers, one or more first linker molecules, one or more second linker molecules and one or more modulators.

In another embodiment, the invention encompasses a method for the preparation of a conjugate complex including:

(i) one or more non-nucleic acid receptors capable of specifically binding an analyte;

(ii) one or more nucleic acid markers including a predetermined nucleotide sequence;

(iii) one or more first linker molecules adapted to bind the non-nucleic acid receptor and the nucleic acid marker;

(iv) one or more nucleic acid oligomers adapted to bind the first linker molecules, wherein the one or more nucleic acid oligomers comprise two complementary nucleic acid strands distinct from the nucleic acid marker; and (v) one or more organic polymers, polynucleotides distinct from the nucleic acid marker and the one or more nucleic acid oligomers, polypeptides or polysaccharides adapted to bind the first linker molecules;

wherein the method comprises the steps of:

(a) contacting one nucleic acid strand of the one or more nucleic acid oligomers with one or more first linker molecules to form a first conjugate of one or more first linker molecules and one nucleic acid strand of the one or more nucleic acid oligomers;

(b) contacting the nucleic acid strand of the one or more nucleic acid oligomers complementary to that used in step (a) with one or more first linker molecules to form a second conjugate of one or more first linker molecules and one nucleic acid strand of the one or more nucleic acid oligomers complementary to that used in step (a);

(c) contacting the conjugate of step (a) with one or more nucleic acid markers to form a first complex of one or more first linker molecules conjugated to one nucleic acid strand of the one or more nucleic acid oligomers and one or more nucleic acid markers;

(d) contacting the conjugate of step (b) with one or more non-nucleic receptors to form a second complex of one or more first linker molecules conjugated to one nucleic acid strand of the one or more nucleic acid oligomers complementary to that used in step (a) and (c) and one or more non-nucleic acid receptors;

(e) contacting the first complex of step (c) with one or more organic polymers, polynucleotides, polypeptides or polysaccharides, to form a third complex of one or more first linker molecules conjugated to one nucleic acid strand of the one or more nucleic acid oligomers, one or more nucleic acid markers and one or more organic polymers, polynucleotides, polypeptides or polysaccharides; and (f) contacting the second complex of step (d) with the third complex of step (e) to form a complex conjugate of one or more first linker molecules conjugated to one nucleic acid strand of the one or more nucleic acid oligomers, one or more nucleic acid markers, one or more organic polymers, polynucleotides, polypeptides or polysaccharides, one or more first linker molecules conjugated to one nucleic acid strand of the one or more nucleic acid oligomers complementary to that used in step (a) and (c) and one or more non-nucleic acid receptors.

In one embodiment of the invention, this method may further include the step of contacting the complexes of steps (d) and (e) with one or more modulators adapted to bind to the first linker molecule before step (f).

In the methods of the invention, the non-nucleic acid receptor, the nucleic acid marker, the first linker molecule, the second linker molecule and the modulator may be as defined above. In particular, the binding of the non-nucleic acid receptor, the nucleic acid marker and the second linker molecule to the first linker molecule may be facilitated by one or more binding partner(s) of the first linker molecule coupled to the non-nucleic acid receptor, the nucleic acid marker and the second linker molecule. In one embodiment, these binding partners are biotin and/or a biotin analog and the first linker molecule is streptavidin, avidin or a biotin-binding fragment thereof.

Also encompassed by the present invention are the conjugate complexes obtainable by the invented methods.

In another aspect, the invention is also directed to the use of the conjugate complex according to the invention in an immunoassay for the detection or the determination of the amount of an analyte. The analyte may be as defined above and is specifically recognized and bound by the non-nucleic acid receptor. The immunoassay may include a nucleic acid amplification reaction to amplify the nucleic acid marker. The amplification reaction is preferably a polymerase chain reaction (PCR), more preferably a real-time PCR reaction.

In still another aspect, the invention features a method for detecting an analyte in a sample, wherein the method includes the steps of:

(a) contacting a conjugate complex according to the invention comprising one or more non-nucleic acid receptors capable of specifically binding said analyte with said sample to form a complex of said analyte and said conjugate complex;

(b) specifically detecting the presence of the one or more nucleic acid markers in said complex;

wherein the presence of the one or more nucleic acid markers indicates the present of the analyte in said sample.

In one embodiment of the present invention, the detecting step (b) may comprise amplifying the one or more nucleic acid markers in a PCR reaction, preferably a real time PCR reaction.

In one embodiment, the detection of the analyte includes the determination of the amount of the analyte, that is a quantitative determination of the analyte.

Detection and, in a specific embodiment, also quantitation of the analyte may be achieved by detection and, optionally, quantitation of the number of amplicons generated in the PCR reaction using the nucleic acid marker as a template. Detection and, optionally quantitation may be achieved by using nucleic acid probes labeled with a detectable label or suitable dyes.

In one embodiment of the invention, the nucleic acid marker is detected by real time PCR, carried out in a commercially available instrument. Real-time PCR amplification is performed in the presence of a fluorescent-labelled probe which specifically binds to the amplified PCR product, for example a dual labelled primer including a fluorescent moiety quenched by another label which is in spatial proximity to the fluorescent label as long as the primer is not incorporated in an amplification product and separated from each other due to elongation of the primer during amplification.

In another embodiment, a non-primer detectable probe which specifically binds the PCR amplification product is used. The probe may include a covalently bonded reporter dye at the 5'-end and a downstream quencher dye at the 3'-end, which allow fluorescent resonance energy transfer (FRET).

Detection of the amplified PCR product may be carried out after each amplification cycle, as the amount of PCR product is at every stage of the amplification reaction proportional to the initial number of template copies. The number of template copies can be calculated by means of the detected fluorescence of the reporter dye. In an intact probe the fluorescence is quenched due to the close proximity of the reporter dye and quencher dye. During PCR, the nuclease activity of the DNA polymerase cleaves the probe in the 5'-3' direction and thus separates the reporter dye from the quencher dye. Because reporter and quencher dye are then no longer in close proximity to each other, the fluorescence of the reporter dye is increased. The increase in fluorescence is measured and is directly proportional to the amplification during PCR. See Heid et al. (1996), "Real time quantitative PCR" Genome Research 6(10):986-994. This detection system is now commercially available as the TaqMan® PCR system from Perkin-Elmer, which allows real time PCR detection.

In an alternative embodiment, the reporter dye and quencher dye may be located on two separate probes which hybridize to the amplified PCR detector molecule in adjacent locations sufficiently close to allow the quencher dye to quench the fluorescence signal of the reporter dye (Rasmussen et al. (1998), "Quantitative PCR by continuous fluorescence monitoring of a double strand DNA specific binding dye" Biochemica 2:8-15). As with the detection system described above, the 5'-3' nuclease activity of the polymerase cleaves the one dye from the probe containing it, separating the reporter dye from the quencher dye located on the adjacent probe preventing quenching of the reporter dye. As in the embodiment described above, detection of the PCR product is by measurement of the increase in fluorescence of the reporter dye.

In other embodiments of this invention, other real time PCR detection strategies may be used, including known techniques such as intercalating dyes (ethidium bromide) and other double stranded DNA binding dyes used for detection (e.g. SYBR green, FMC Bioproducts), dual fluorescent probes (Wittwer et al. (1977) BioTechniques 22: 130-138 and Wittwer et al. (1997) BioTechniques 22: 176-181) and panhandle fluorescent probes (i.e. molecular beacons; Tyagi and Kramer (1996) Nature Biotechnology 14: 303-308). Although intercalating dyes and double stranded DNA binding dyes permit quantitation of PCR product accumulation in real time applications, they suffer from a lack of specificity, detecting primer dimer and any non-specific amplification product. Careful sample preparation and handling, as well as careful primer design, using known techniques are necessary to minimize the presence of matrix and contaminant DNA and to prevent primer dimer formation. Appropriate PCR instrument analysis software and melting temperature analysis permit a means to extract specificity (Ririe, K., et al. (1977) Anal. Biochem. 245: 154-160) and may be used with these embodiments.

In still another embodiment of this invention, the Scorpions reaction is used as a real time PCR detection method. Scorpions are bi-functional molecules containing a PCR primer covalently linked to a probe. The fluorophore in the probe interacts with a quencher which reduces fluorescence. During the PCR reaction the primer binds to the template and is elongated by the polymerase. Once the elongation reaction is completed and primer and template are separated in the denaturation step, the elongated primer sequence can interact intramolecularly with the probe sequence in the next annealing step. The binding of the probe to the elongated primer sequence prevents interaction of the probe-bound fluorophore with the quencher, which leads to an increase in light output from the reaction tube. Currently, there are two formats for Scorpions, the bimolecular Scorpion format and the unimolecular format. In the bimolecular format the quencher is bound to a separate nucleic acid molecule which is complementary to the probe sequence, whereas in the unimolecular format both, fluorophore and quencher, are attached to the same molecule, and an integral stem loop sequence is used to bring the quencher close to the fluorophore.

The Scorpions technique is described more fully in Whitcombe et al. (1999), Detection of PCR products using self-probing amplicons and fluorescence, *Nature Biotech* 17, pages 804-807. This detection system is now commercially available as the scorpions system from DxS Ltd. (Manchester, UK).

The design of primers for the amplification reaction and nucleic acid probes is well-established in the art and thus routine practice for the skilled person. Suitable fluorescent reporter dyes are also known and commercially available, and include, without limitation 6-carboxy-fluorescein (FAM), tetrachloro-6-carboxy-fluorescein (TET), 2,7-dimethoxy-4,5-dichloro-6-carboxy-fluorescein (JOE) and hexachloro-6-carboxy-fluorescein (HEX). Another suitable reporter dye is 6-carboxy-tetramethyl-rhodamine (TAMRA).

The test sample may be any sample, but is preferably of biological origin, for example a biological sample from a human. In one specific example, the sample is a tissue sample, a body fluid sample or a cell sample.

In another aspect, the invention relates to a kit including one or more conjugate complexes according to the invention or manufactured according to the methods of the invention. Such a kit may additionally contain further components. Exemplary components that may be additionally comprised in the kits of the present invention include, but are not limited to buffers, dyes, oligonucleotide primers or probes, which may be optionally labeled with a detectable label, etc. The components of the conjugate complexes according to the invention may be as defined above.

In still another aspect, the invention is also directed to the use of one or more organic polymer, polypeptide, polysaccharide and/or oligo- or polynucleotide molecules, all of which may be optionally biotinylated, as additional linker molecules in a conjugate comprising one or more non-nucleic acid receptors, one or more nucleic acid markers and one or more first linker molecules to form a conjugate complex comprising one or more non-nucleic acid receptors, one or more nucleic acid markers, one or more first linker molecules and one or more organic polymer, polypeptide, polysaccharide and/or oligo- or polynucleotide molecules.

The inventions illustratively described herein may suitably be practiced in the absence of any element or elements, limitation or limitations, not specifically disclosed herein. Thus, for example, the terms "comprising", "including", "containing", etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention has been specifically disclosed by specific embodiments and optional features, modification and variation of the inventions embodied therein herein disclosed may be resorted to by those skilled in the art, and that such modifications and variations are considered to be within the scope of this invention.

The content of all patent documents cited herein is incorporated by reference in their entirety.

The invention has been described broadly and generically herein. Each of the narrower species and subgeneric groupings falling within the generic disclosure also form part of the invention. This includes the generic description of the invention with a proviso or negative limitation removing any subject matter from the genus, regardless of whether or not the excised material is specifically recited herein.

Other embodiments are within the following claims and non-limiting examples. In addition, where features or aspects of the invention are described in terms of Markush groups, those skilled in the art will recognize that the invention is also thereby described in terms of any individual member or subgroup of members of the Markush group.

EXAMPLES

Example 1

Synthesis of Polybiotin Conjugate Complexes ("PBC")

0.183 g Polyethylenimine ("PEI" Aldrich 40.872-7, m-w. 25,000 branched chain polymer with 1:2:1 primary:secondary:tertiary amines) were heated to 40° C. and added to 10 ml PBS for an 106 nmol/µl solution of primary amines. 3.71 NHS-Biotin (Sigma, B-1022) were dissolved in 62.6 ml DMF for a 106 nmol/µl solution of NHS-Biotin. 10 µl of the NHS-Biotin-solution were incubated for 30 min at RT with 40 µl of the PEI solution for a 1+4 excess of free amino groups. Finally, 1 ml of PBS was added to the reaction mixture and the product was purified by subsequently using a microfiltration column (centricon 30) and a NAP10 column according to manufacturer's instructions. The synthesized polybiotin-conjugate ("PBC") was stored in PBS (20 mM phosphate, 50 mM NaCl) at a concentration of 1 nmol/µl PEI.

Functionality of the conjugate was tested by adding PBC to a 2:1 mixture of STV and bis-biotinylated 169 bp DNA (DNA-marker "1" (SEQ ID NO:1)) and subsequent gel electrophoresis: In the presence of PBC, only a single, immobile lane of polymerized DNA was observed in contrast to the multiple lane pattern normally typical for a 2:1 mixture of STV and biotinylated DNA, indicating the formation of supramolecular conjugate complexes.

TABLE 1

Different kinds of PBC and their influence on the crosslinking of STV-DNA-networks

| | DNA + STV | DNA + STV + Biotin-BSA (Sigma) | DNA + STV + PBC (with Biotin:PEI 1:4) |
|---|---|---|---|
| DNA in ladder-pattern of typical DNA-STV conjugates | 100% | 50% | 0% |
| DNA in immobile lane of large polymerized conjugates | 0% | 50% | 100% |

Example 2

Application of Anti-Rabbit Conjugate Complexes ("ARC")

30 µl of a 2.11 pmol/ml solution of 169 bp bis-biotinylated DNA (DNA-marker "1" (SEQ ID NO:1); 63.3. pmol) were incubated for 30 min at RT with 3.24 µl of a 19.5 pmol/µl solution of recombinant streptavidin (IBA) to form a STV-DNA conjugate ("SDC"). 30 µl of this SDC were mixed with 30 µl of a 500 µg/ml solution of biotinylated Goat-anti-Rabbit-IgG (Fab)$_2$-fragments and incubated for 60 min at RT/orbital shaking. The antibody-DNA-STV conjugate was purified by FPLC (Superdex® 200 resin, Amersham Biosciences, Inc.) and the 1 ml product fraction was mixed with 2 ml NaCl solution. (300 mM) for a final solution of 10.5 pmol/ml anti-rabbit DNA conjugate ("ARC") (cf. Niemeyer et al., (1999). Nucleic Acids Res 27(23): 4553-61).

Nunc TopYield™ modules were coated overnight at 4° C. with 30 µl/well of a dilution series of rabbit IgG (Sigma) in borate buffer and subsequently blocked overnight at 4° C. against unspecific interactions with 240 µl/well of a TBS buffer containing 4.5% Skim milk powder, 5 mM EDTA, 1 mg/ml salmon sperm DNA and 0.2% NaN$_3$. The modules were washed 5 times with TBS containing 5 mM EDTA and 0.05% Tween® 20 surface active agent (ICI Americas Inc.) ("TETBS") and incubated with a solution of a.) 2.4 µl of ARC, mixed with 240 µl TBS buffer ("ARC"); or b.) 2.4 µl of ARC, mixed with 1.2 µl of PBC(1:4) (generated according to Example 1) and 240 µl TBS buffer ("ARC-2"); or c.) 2.4 µl of ARC, mixed with 0.1 µl of PBC(1:4) (generated according to Example1) and 240 µl TBS buffer ("ARC-3")

30 µl/well for 25 min at RT/orbital shaking.

Finally, the modules were washed 7 times with TETBS and 3 times with TBS. 30 µl of a PCR mastermix containing digoxigenin-labelled dUTP and two biotinylated primers were added to each well and a standard PCR (28 cycles, 50° C./72° C./95° C.) was performed for amplification of the DNA marker included in the ARC conjugate. The utilized amplification primers had the nucleotide sequences set forth in SEQ ID NO:3 and SEQ ID NO:4.

The biotin- and digoxigenin labelled DNA amplicons were subsequently immobilized on STV-coated microplates and detected with PCR-ELISA by using an anti-digoxigenin-alkaline-phosphatase conjugate and the fluorescence generating substrate AttoPhos® (JBL Scientific Inc.) as described in more detail in Niemeyer et al. (Niemeyer et al. (1997). Anal Biochem 246(1): 140-5).

The results shown in FIG. 1 demonstrated the increased performance of the ARC-2 conjugate (containing the additional polybiotinylated linker molecule PBC) compared to the standard ARC conjugate.

Example 3

Detection of Mistletoe Lectin

Different detection conjugates for mistletoe lectin were prepared:

a.) 195 pmol STV+97.5 pmol double biotinylated DNA (DNA-marker "1" (SEQ ID NO:1)) were mixed in 50 µl TE, 25 µl of this mixture were incubated for 15 min at RT with 90 pmol of a biotinylated polyclonal rabbit-anti-mistletoe-lectin antibody ("T2", Viscum AG). The conjugate was purified by FPLC and stored in working aliquots at −80° C.: "Standard-Conjugate 1"

195 pmol STV+97.5 pmol double biotinylated 169 bp DNA (SEQ ID NO:1) were mixed in 50 µl TE, 25 µl of this mixture were incubated for 15 min at RT with 90 pmol of a biotinylated polyclonal rabbit-anti-lectine antibody. Subsequently, 20 pmol of polybiotylated BSA (Sigma) was added and the mixture was incubated for another 10 min RT. The conjugate was purified by FPLC and stored in working aliquots at −80° C.: "Enhanced-Conjugate 2"

b.) Same preparation as b.), exception: 450 pmol of a biotinylated polyclonal rabbit-anti-lectin antibody: "Enhanced-Conjugate 3"

c.) Same preparation as b.), exception: 97.5 pmol of polybiotylated BSA (Sigma): "Enhanced-Conjugate 4"

d.) Same preparation as c.), exception: 97.5 pmol of polybiotylated BSA (Sigma): "Enhanced-Conjugate 5"

TopYield™ modules (Nunc) were coated overnight at 4° C. with 30 µl/well polyclonal rabbit-anti-mistletoe-lectin antibody (1 mg/ml) and subsequently blocked against unspecific interactions with 240 µl/well of a TBS buffer containing 4.5% Skim milk powder, 5 mM EDTA, 1 mg/ml salmon sperm DNA and 0.2% NaN$_3$. The modules were washed 5 times with TBS containing 5 mM EDTA and 0.05% Tween® 20 surface active agent (ICI Americas Inc.) ("TETBS") and incubated of a dilution series of recombinant mistletoe lectin in standardized human serum ("BISEKO®", Biotest, Germany) for 25 min/RT. Concentrations: 400 pg/ml, 13.2 pg/ml and 400 fg/ml; additionally a NC of BISEKO® without spiked antigen.

Following another 5-fold washing step, the modules were incubated with 30 µl/well of a 1:100 dilution of either conjugate in TETBS for 25 min/RT. After a final washing step, consisting of 7 times 240 ml/well TETBS and 3 times 240 ml/well TBS, 30 µl of a real-time PCR mastermix containing a TaqMan® probe (Roche Molecular Systems, Inc.) specific for the DNA template and two specific primers (SEQ ID NO:3 and SEQ ID NO:4) were added to each well and a modified real-time PCR (40 cycles, 30 sec 72° C., 12 sec 95° C., 30 sec 50° C. in each cycle) was performed for combined amplification and detection of the DNA marker by using an ABI-Prism® 7000 instrument (Applera Corp.).

Increase of fluorescence during PCR was recorded and analyzed according to well-established procedures (See Adler and Niemeyer (2004) *Enhanced Protein Detection Using Real-Time Immuno-PCR*, in *DNA Amplification—Current Technologies and Applications*, V. V. Demidov and N. E. Broude, Editors. 2004, Horizon Bioscience: Norfolk. p. 293-312).

Figure 2:
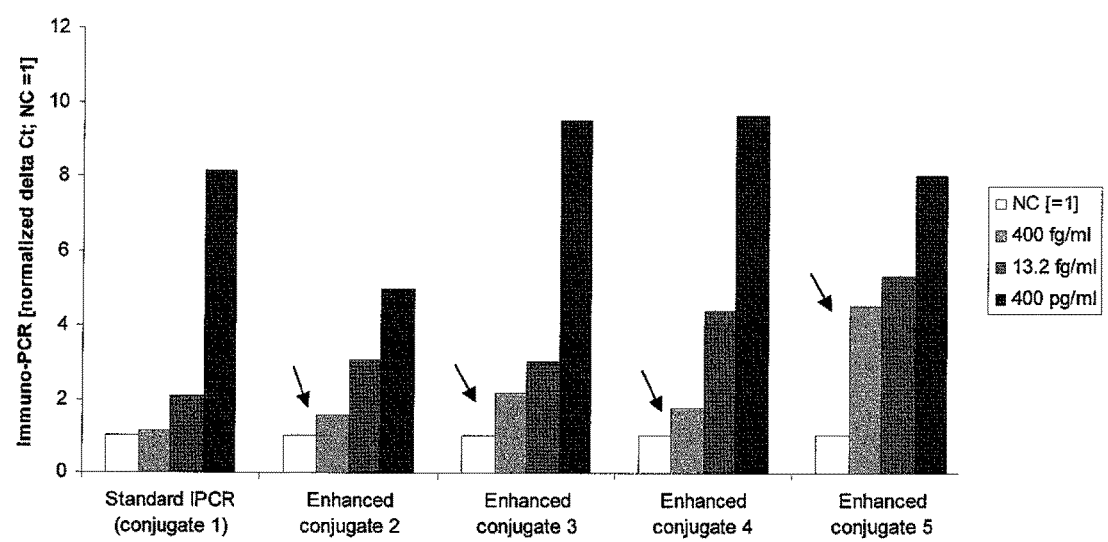
FIG. 2 shows the signal intensity of an IPCR assay for the detection of mistletoe lectin for a standard IPCR conjugate and different enhanced conjugates prepared with an additional polybiotinylated BSA linker molecule according to the invention.

The results as shown in FIG. 2 revealed the superiority of the enhanced conjugates 2-5 compared to the standard conjugate 1. An enhanced conjugates revealed a significantly improved signal-to-background ratio especially for the lowest spiked concentrations.

Example 4

Construction and Application of a Hybrid-Conjugate a.) Complimentary STV-Oligonucleotide adaptors were prepared according to well-known protocols (Kukolka et al. (2004) *Methods Mol. Biol.* 283:181-96). Briefly, thiolated DNA-fragments were connected to STV by use of a heterobifunctional crosslinker. For complimentary conjugates, the sequences "A" (SEQ ID NO:7) and "cA" (SEQ ID NO:8) were linked to STV, forming the hybrid adaptors "HA" and "HcA", respectively.

A 10 pmol/µl solution of the adaptors in Tris buffer including 5 mM EDTA ("TE") was prepared as working aliquots.

b.) The hybrid adaptor "HA" was integrated in a DNA-network by subsequent addition of
  i.) double biotinylated DNA (DNA-marker "2" (SEQ ID NO:2) equimolar ratio, incubation time: 10 min RT/orbital shaking)
  ii.) poly-biotinylated linker (see example 1) (equimolar ratio, incubation time: 15 min RT/orbital shaking)
  iii.) amino-modified biotin (5fold excess to biotin-binding sites in free STV=20fold excess to STV or DNA, incubation time: 10 min RT/orbital shaking).

c.) The hybrid adaptor "HcA" was coupled with a biotinylated antibody against rabbit-IgG by subsequent addition of
  i.) biotinylated antibody goat-anti-rabbit IgG (Sigma) (2fold excess, incubation time: 10 min RT/orbital shaking)
  ii.) amino-modified biotin (5-fold excess to biotin-binding sites in free STV=20-fold excess to STV or DNA, incubation time 10 min RT/orbital shaking).

d.) The product conjugates of b.) and c.) were mixed for hybridization-coupling of DNA-networks and detection antibodies (equimolar ratio). Hybridization was carried out in a concentration of 200 mM of the conjugates (in regard to STV-oligonucleotide adaptors) and performed in hybridization buffer, consisting of Tris buffer, 0.05% Tween® 20 surface active agent (ICI Americas Inc.), 5 mM EDTA, biotin, 0.5% skim milk powder and 0.1 mg/ml salmon sperm DNA for 25 min RT and orbital shaking.

e.) The product mixture of step d.) was incubated in a 1:300 dilution in hybridization buffer on rabbit-IgG coated TopYield modules. These modules were prepared by:
  i) preparing a 5 fmol/30 µl-5 zmol/30 µl dilution series of rabbit-IgG in borate buffer and incubation of this dilution series overnight at 4° C. on TopYield™ modules (Nunc)
  ii) subsequent 3 times washing of the modules 3 times with TBS buffer
  iii) overnight blocking at 4° C. with 240 µl/well blocking reagent (TBS buffer containing 4.5% Skim milk powder, 5 mM EDTA, 1 mg/ml salmon sperm DNA and 0.2% $NaN_3$) and finally
  iv) washing 4 times with TETBS (TBS containing 5 mM EDTA and 0.05% Tween® 20 surface active agent (ICI Americas Inc.)).

Incubation of the detection reagent was carried out with 30 µl/well and 30 min incubation time at RT/orbital shaking.

Parallel control experiments were carried out by using
  i) a detection conjugate prepared according to steps a.)-d.), but without added polybiotinylated linker (step b-ii) and the use of biotin instead of amino-biotin (step b-iii and c-ii)
  ii) conventional sequential incubation of biotinylated goat-anti-rabbit detection antibody, STV and biotinylated DNA as described for Universal-IPCR (Zhou et al. (1993) *Nucleic Acids Res.* 21(25):6038-9).

f.) The modules were washed 7 times with TETBS and 2 times with TBS (240 µl/well, 2.5 min washing time for each washing step) and 30 µl/well of a real-time PCR mastermix containing a TaqMan® probe (Roche Molecular Systems, Inc.) specific for the DNA template and two specific primers (SEQ ID NO:5 and SEQ ID NO:6) was added to each well. Then modules were sealed with adhesive foil and placed in an ABI-Prism® 7000 instrument (Applera Corp.) for DNA-amplification.

PCR-programme: (40 cycles, 12 sec 72° C., 12 sec 95° C., 12 sec 50° C. in each cycle).

Increase of fluorescence during PCR was recorded and analyzed according to well-established procedures (See Adler and Niemeyer (2004), supra).

Figure 3:
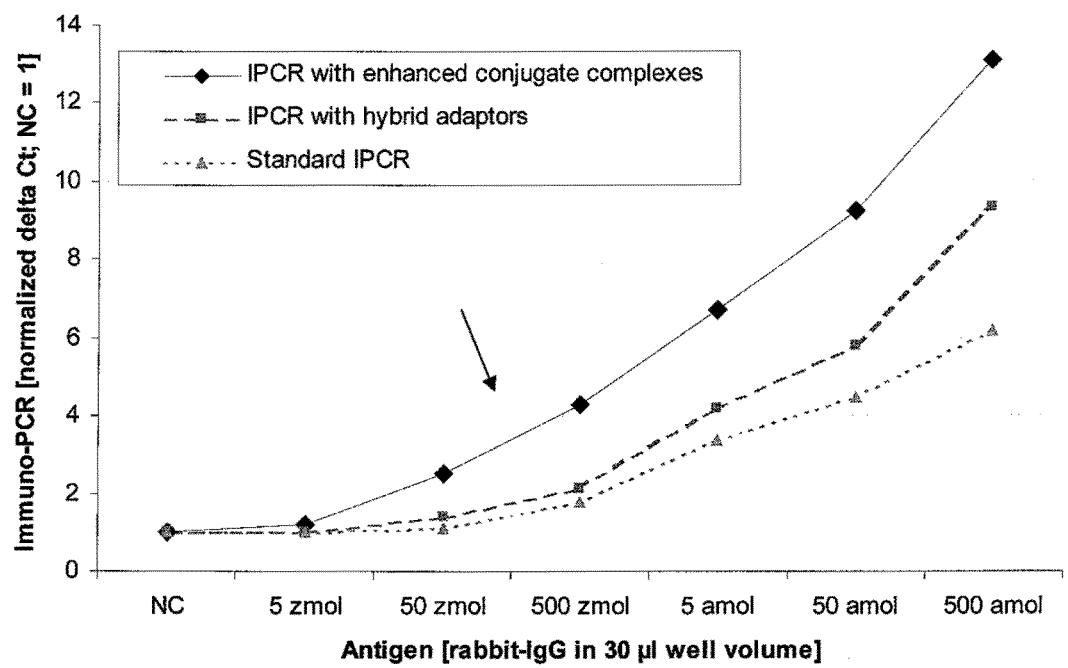
FIG. 3 shows the signal intensity of an IPCR assay for the detection of rabbit-IgG for a standard sequential IPCR, a conventional hybrid conjugate and novel enhanced hybrid conjugates prepared with additional polybiotinylated liker and adaptor molecules according to the invention.
Figure 4:
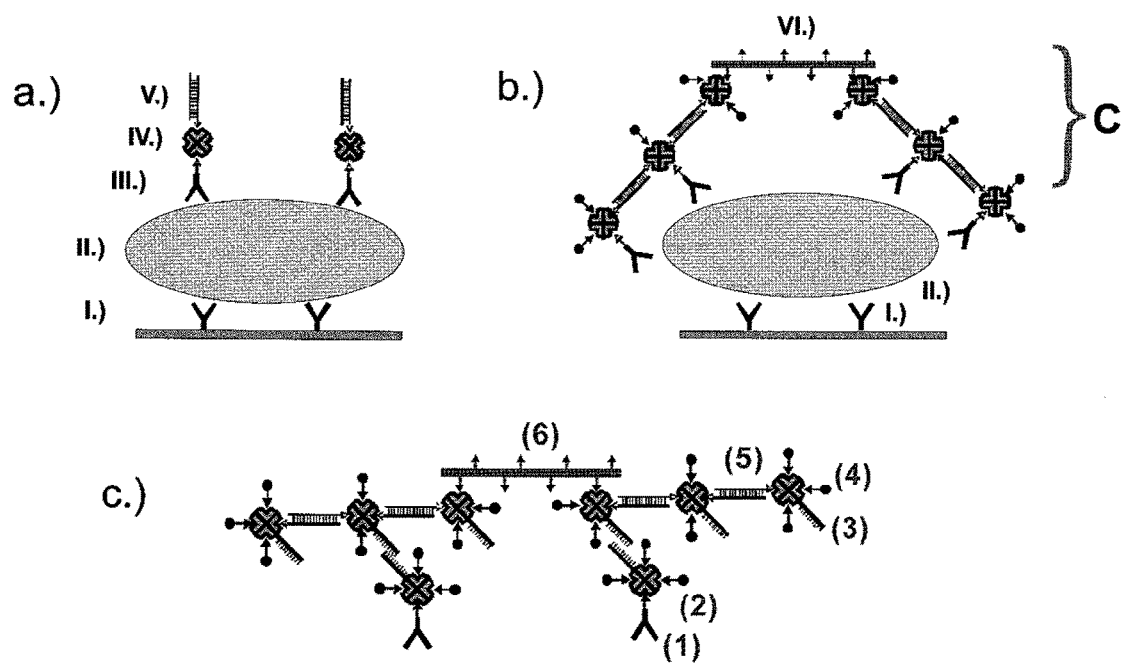
FIG. 4 shows a schematic drawing of a.) conventional sequential Immuno-PCR (I capture antibody, II antigen, III biotinylated detection antibody, IV STV, V biotinylated DNA) compared to the application of b.) enhanced conjugates including a second linker (I capture antibody, II antigen, "C"=conjugate including VI second linker) and c.) enhanced hybrid conjugates consisting of (1) biotinylated detection antibody, (2) DNA-STV adaptor, (3) complementary DNA-STV adaptor, (4) amino-biotin, (5) biotinylated DNA, (6) biotinylated second linker. The schematic drawings are simplified for clarity purposes as typically more compounds are interconnected in a 3-dimensional network.

The results as shown in FIG. 3 show increased sensitivity and signal-to-background ratio for the enhanced detection conjugates including amino-biotin and additional second linker compared to standard sequential IPCR (Zhou et al., supra) and conventional hybrid conjugates (Niemeyer et al. *Bioconjug Chem*, 2001. 12, 3. p. 364-71).

We claim:

1. A conjugate complex for binding to an analyte of interest, comprising:
   (a) at least two non-nucleic acid receptors that specifically bind the analyte;
   (b) at least two nucleic acid markers comprising a predetermined nucleotide sequence;
   (c) at least two first linker molecules, wherein each linker molecule specifically binds the non-nucleic acid receptor and the nucleic acid marker; and
   (d) at least two second linker molecules that specifically binds the first linker molecules, wherein the at least two non-nucleic receptors and the at least two nucleic acid markers are each coupled to one or more binding partners of the first linker molecule to facilitate binding of the at least two non-nucleic receptors and the at least two nucleic acid markers to the at least two first linker molecules, wherein the at least two second linker molecules are each coupled to one or more binding partners of the first linker molecule to facilitate binding of the at least two second linker molecules to the at least two first linker molecules, wherein the at least two first linker molecules and the at least two second linker molecules are at least bivalent.

2. A conjugate complex according to claim 1, wherein the binding of the at least two first linker molecules to the non-nucleic acid receptor, the nucleic acid marker and/or the second linker molecule is non-covalent.

3. A conjugate complex according to claim 1, wherein the at least two second linker molecules are organic polymers, proteins, polysaccharides, or mixtures thereof.

4. A conjugate complex according to claim 1, wherein the at least two second linker molecules are organic polymer molecules selected from the group of linear or branched polyethyleneimines, polyacrylamides, polyamines, and polyamidoamines.

5. A conjugate complex according to claim 1, wherein the at least two second linker molecules are proteins selected from the group consisting of albumines, immunoglobulins and poly-amino acids.

6. A conjugate complex according to any one of claim 1, wherein the at least two second linker molecules are polysaccharides selected from the group of linear dextrans, cyclic dextrans and branched dextrans.

7. A conjugate complex according to claim 1, wherein the at least two second linker molecules are nucleic acids selected from the group consisting of nucleic acid oligomers consisting of two complementary nucleic acid strands, wherein each of the complementary nucleic acid strands binds a first linker molecule, and polynucleotides.

8. A conjugate complex according to claim 1, wherein at least two second linker molecules are nucleic acid oligomers consisting of two complementary nucleic acid strands, wherein the complementary nucleic acid strands binds the first linker molecule.

9. A conjugate complex according to claim 1, wherein the at least two second linker molecules are a combination of two or more different molecules selected from the group consisting of linear, branched or dendritic polyethyleneimines, polyacrylamides, polyamines, polyamidoamines, albumines, immunoglobulins, poly-amino acids, linear dextrans, cyclic dextrans, branched dextrans, polynucleotides, and nucleic acid oligomers consisting of two complementary nucleic acid strands.

10. A conjugate complex according to claim 1, wherein the at least two non-nucleic receptors and the at least two nucleic acid markers are each coupled to at least two binding partners of the first linker molecule that facilitate binding of the at least two non-nucleic acid receptors and the at least two nucleic acid markers to the at least two first linker molecules.

11. A conjugate complex according to claim 10, wherein the at least two binding partners of the first linker molecule coupled to the at least two non-nucleic acid receptors and the one or more nucleic acid markers are the same or different.

12. A conjugate complex according to claim 10, wherein the at least two binding partners of the first linker molecule are covalently coupled to the at least two non-nucleic acid receptors and the nucleic acid markers.

13. A conjugate complex according to claim 1, wherein the at least two second linker molecules are each coupled to at least two binding partners of the first linker molecule.

14. A conjugate complex according to claim 13, wherein the at least two binding partners of the first linker molecule are covalently coupled to the at least two second linker molecules.

15. A conjugate complex according to claim 10, wherein the binding of the at least two binding partners of the first linker molecule to the first linker molecule is non-covalent.

16. A conjugate complex according to claim 10, wherein the first linker molecule is avidin or streptavidin or a biotin-binding fragment or mutant thereof.

17. A conjugate complex according to claim 10, wherein the binding partner of the first linker molecule is biotin or a biotin analog.

18. A conjugate complex according to claim 1, wherein the non-nucleic receptor is an antibody or antibody fragment.

19. A conjugate complex according to claim 1, wherein the analyte is an antigen or hapten.

20. A conjugate complex according to claim 1 further comprising at least two modulators that specifically bind to the at least two first linker molecules to saturate non-occupied binding sites of the first linker molecule for the non-nucleic acid receptor, the nucleic acid marker, the second linker molecule, or a binding partner of the first linker molecule.

21. A conjugate complex according to claim 20, wherein the at least two modulators are positively charged.

22. A conjugate complex according to claim 20, wherein the at least two modulators are amino-biotin, diamino-biotin or amino-substituted biotin analogs.

23. A conjugate complex according to claim 1, wherein the nucleic acid marker is dsDNA, ssDNA, dsRNA, ssRNA or a DNA:RNA hybrid.

24. A method for the preparation of a conjugate complex according to claim 1, comprising the steps of:
 (a) contacting at least two nucleic acid markers with at least two first linker molecules, wherein each first linker molecule specifically binds the at least two nucleic acid markers to form a complex of at least two nucleic acid markers with at least two first linker molecules;
 (b) contacting the complex of step (a) with at least two non-nucleic acid receptors, wherein each non-nucleic acid receptor specifically binds the at least two first linker molecules to form a complex of at least two non-nucleic acid receptors, at least two nucleic acid markers and at least two first linker molecules; and
 (c) contacting the complex of step (b) with at least two second linker molecules that specifically bind the at least two first linker molecules to form a complex of at least two non-nucleic acid receptors, at least two nucleic acid markers, at least two first linker molecules and at least two second linker molecules.

25. A method according to claim 24, further comprising the step of:
 (d) contacting the complex of step (c) with at least two modulators that specifically bind the at least two first linker molecules to saturate non-occupied binding sites of the first linker molecule for the non-nucleic acid receptor, the nucleic acid marker and the second linker molecule to form a complex of at least two non-nucleic acid receptors, at least two nucleic acid markers, at least two first linker molecules, at least two second linker molecules and at least two modulators.

26. A method for the preparation of a conjugate complex that binds an analyte of interest, comprising
 (i) at least two non-nucleic acid receptors that specifically binds the analyte;
 (ii) at least two nucleic acid markers comprising a predetermined nucleotide sequence;
 (iii) at least two first linker molecules, wherein each linker molecule specifically binds the non-nucleic acid receptor and the nucleic acid marker;
 (iv) at least two nucleic acid oligomers that specifically bind at least two first linker molecules, wherein the at least two nucleic acid oligomers comprise two complementary nucleic acid strands distinct from the nucleic acid marker; and
 (v) at least two organic polymers, polynucleotides, proteins or polysaccharides that specifically bind at least two first linker molecules, wherein the polynucleotides of (v) are distinct from the nucleic acid marker and the at least two nucleic acid oligomers;

wherein the method comprises the steps of:

(a) contacting one nucleic acid strand of the at least two nucleic acid oligomers with at least two first linker molecules to form a first conjugate of at least two first linker molecules and one nucleic acid strand of the at least two nucleic acid oligomers;

(b) contacting the nucleic acid strand of the at least two nucleic acid oligomers complementary to that used in step (a) with at least two first linker molecules to form a second conjugate of at least two first linker molecules and one nucleic acid strand of the at least two nucleic acid oligomers complementary to that used in step (a);

(c) contacting the conjugate of step (a) with at least two nucleic acid markers to form a first complex of at least two first linker molecules conjugated to one nucleic acid strand of the at least two nucleic acid oligomers and at least two nucleic acid markers;

(d) contacting the conjugate of step (b) with at least two non-nucleic receptors to form a second complex of at least two first linker molecules conjugated to one nucleic acid strand of the at least two nucleic acid oligomers complementary to that used in step (a) and (c) and at least two non-nucleic acid receptors;

(e) contacting the first complex of step (c) with at least two organic polymers, polynucleotides, proteins or polysaccharides, to form a third complex of at least two first linker molecules conjugated to one nucleic acid strand of the at least two nucleic acid oligomers, at least two nucleic acid markers and at least two organic polymers, polynucleotides, proteins or polysaccharides; and (f) contacting the second complex of step (d) with the third complex of step (e) to form the complex conjugate of at least two first linker molecules conjugated to one nucleic acid strand of the at least two nucleic acid oligomers, at least two nucleic acid markers, at least two organic polymers, polynucleotides, proteins or polysaccharides, at least two first linker molecules conjugated to one nucleic acid strand of the at least two nucleic acid oligomers complementary to that used in step (a) and (c) and at least two non-nucleic acid receptors.

27. A method according to claim 26, wherein the method further comprises the steps of contacting the complexes of steps (d) and (e) with at least two modulators that specifically bind at least two first linker molecules before step (f).

28. A method for detecting an analyte in a sample, the method comprising the steps of:

(a) contacting the conjugate complex of claim 1 comprising at least two non-nucleic acid receptors that specifically bind said analyte with said sample to form a complex of said analyte and said conjugate complex;

(b) specifically detecting the presence of the at least two nucleic acid markers in said complex;

wherein the presence of the at least two nucleic acid markers indicates the present of the analyte in said sample.

29. A method according to claim 28, wherein the detecting step (b) comprises amplifying the at least two nucleic acid markers in a PCR reaction.

30. A kit comprising at least two conjugate complexes according to claim 1.

* * * * *

UNITED STATES PATENT AND TRADEMARK OFFICE
CERTIFICATE OF CORRECTION

PATENT NO. : 8,927,210 B2  
APPLICATION NO. : 12/622686  
DATED : January 6, 2015  
INVENTOR(S) : Adler et al.

Page 1 of 1

It is certified that error appears in the above-identified patent and that said Letters Patent is hereby corrected as shown below:

In the specification

Column 13, line 47, delete the text "to" and replace with --two--.

Signed and Sealed this
First Day of March, 2016

Michelle K. Lee
*Director of the United States Patent and Trademark Office*